United States Patent
Maar

(10) Patent No.: US 11,104,938 B2
(45) Date of Patent: Aug. 31, 2021

(54) DIGITAL AMPLIFICATION ASSAYS FOR GENETIC INSTABILITY

(71) Applicant: Bio-Rad Laboratories, Inc., Hercules, CA (US)

(72) Inventor: Dianna Maar, Mountain House, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 383 days.

(21) Appl. No.: 16/013,845

(22) Filed: Jun. 20, 2018

(65) Prior Publication Data

US 2018/0363041 A1    Dec. 20, 2018

Related U.S. Application Data

(60) Provisional application No. 62/522,619, filed on Jun. 20, 2017.

(51) Int. Cl.
*C12Q 1/68*       (2018.01)
*C12Q 1/6848*    (2018.01)
(Continued)

(52) U.S. Cl.
CPC ......... *C12Q 1/6848* (2013.01); *C12Q 1/6832* (2013.01); *C12Q 1/6858* (2013.01)

(58) Field of Classification Search
None
See application file for complete search history.

(56) References Cited

U.S. PATENT DOCUMENTS

| | | |
|---|---|---|
| 6,660,477 B2 | 12/2003 | Kluwe |
| 6,780,588 B2 | 8/2004 | Coticone et al. |

(Continued)

FOREIGN PATENT DOCUMENTS

| | | |
|---|---|---|
| EP | 1478781 B1 | 4/2010 |
| WO | 0222879 A2 | 3/2002 |

(Continued)

OTHER PUBLICATIONS

Traverso et al. (The Lancet, 2002, vol. 359, p. 403-404) (Year: 2002).*

(Continued)

*Primary Examiner* — Stephanie K Mummert
(74) *Attorney, Agent, or Firm* — Kolisch Hartwell, P.C.

(57) ABSTRACT

Methods and compositions for detecting genetic instability using digital amplification assays. The methods may be performed in a set of isolated volumes and generally may involve competitive hybridization of a competitor and a probe/primer with a normal allele and one or more mutant alleles of a microsatellite locus. The competitor may be configured to compete similarly with, or to outcompete, the primer/probe for hybridization with the normal allele. The primer/probe may be configured to outcompete the competitor for hybridization with various mutant alleles of the locus that alter the length of the repetitive sequence by different amounts. Isolated volumes in which the primer/probe outcompetes the competitor may be enumerated, and represent one or more of the mutant alleles. The methods may enable diagnosing microsatellite instability and treating a subject based on the diagnosis.

17 Claims, 12 Drawing Sheets

Specification includes a Sequence Listing.

(51) Int. Cl.
*C12Q 1/6832* (2018.01)
*C12Q 1/6858* (2018.01)

(56) References Cited

U.S. PATENT DOCUMENTS

| | | | |
|---|---|---|---|
| 6,841,349 | B2 | 1/2005 | Coticone et al. |
| 7,749,706 | B2 | 7/2010 | Bacher et al. |
| 7,902,343 | B2 | 3/2011 | Bacher et al. |
| 7,977,108 | B2 | 7/2011 | Newhouse et al. |
| 9,868,981 | B2 | 1/2018 | Cooper et al. |
| 9,898,981 | B2 * | 2/2018 | Lee .............. G09G 3/3648 |
| 2004/0142369 | A1 | 7/2004 | Alajem et al. |
| 2007/0092880 | A1 | 4/2007 | Crothers et al. |
| 2013/0099018 | A1 | 4/2013 | Miller et al. |
| 2013/0323727 | A1 | 12/2013 | Huang et al. |
| 2015/0045369 | A1 | 2/2015 | Lambrechts |
| 2016/0362731 | A1 | 12/2016 | Cooper et al. |
| 2017/0032082 | A1 | 2/2017 | Nguyen et al. |

FOREIGN PATENT DOCUMENTS

| | | | |
|---|---|---|---|
| WO | 2012095639 | A2 | 7/2012 |
| WO | WO-2012095639 | A2 * | 7/2012 ........... C12Q 1/6853 |
| WO | 2014074651 | A1 | 5/2015 |
| WO | 2016/077553 | A1 | 5/2016 |
| WO | 2016077553 | A1 | 5/2016 |
| WO | 2018237088 | A1 | 12/2018 |

OTHER PUBLICATIONS

Le et al. (Journal of Clinical Oncology 34, No. 4_suppl, 2017) (Year: 2017).*

Haruma, Tomoko et al., "Clinical impact of endometrial cancer stratified by genetic mutational profiles, POLE mutation, and microsatellite instability", PLOS ONE, published Apr. 16, 2018, 16 pages.

Kok, Marleen et al., "Profound Immunotherapy Response in Mismatch Repair-Deficient Breast Cancer", Case Report, JCO Precision Oncology—ASCO Journals, published Oct. 3, 2017, 3 pages.

Le, Dung T. et al., "Mismatch-repair deficiency predicts response of solid tumors to PD-1 blockade", Science, vol. 357 (6349): 409-413, Jul. 28, 2017, 15 pages.

Overman, Michael J. et al., "Durable Clinical Benefit With Nivolumab Plus Ipilimumab in DNA Mismatch Repair-Deficient/Microsatellite Instability-High Metastatic Colorectal Cancer", Journal of Clinical Oncology, vol. 36, No. 8, Mar. 10, 2018, 18 pages.

Promega Corporation, "MSI Analysis System, Version 1.2" Technical Manual, Revised Nov. 2017, 29 pages.

Young, Lee W., Authorized Officer, ISA/US, Commissioner for Patents, "International Search Report" in connection with related International Application No. PCT/US2018/038622, dated Sep. 20, 2018, 3 pages.

Young, Lee W, Authorized Officer, ISA/US, Commissioner for Patents, "Written Opinion of the International Searching Authority" in connection with related International Application No. PCT/US2018/038622, dated Sep. 20, 2018, 10 pages.

Ginya, Harumi et al., Development of the Handy Bio-Strand and its application to genotyping of OPRM1 (A118G), Analytical Biochemistry, vol. 367, May 6, 2007, pp. 79-86.

Jia, Yanwei et al., "Kinetic Hairpin Oligonucleotide Blockers for Selective Amplification of Rare Mutations", Scientific Reports 4, Article No. 5921, Aug. 1, 2014, 8 pgs.

Sandberg, Scott O., "Quasi-digital PCR: Enrichment and quantification of rare DNA variants", Biomed Microdevices, 16, May 1, 2014, pp. 639-644.

Zhou, Luming et al., "Rare allele enrichment and detection by allele-specific PCR, competitive probe blocking, and melting analysis", Biotechniques 50, May 2011, pp. 311-318.

* cited by examiner

DIGITAL AMPLIFICATION ASSAYS FOR GENETIC INSTABILITY

CROSS-REFERENCE TO PRIORITY APPLICATION

This application is based upon and claims the benefit under 35 U.S.C. § 119(e) of U.S. Provisional Patent Application Ser. No. 62/522,619, filed Jun. 20, 2017, which is incorporated herein by reference in its entirety for all purposes.

INTRODUCTION

A biological sample can be tested for the presence of a target sequence using an amplification assay, which can be performed in bulk phase (e.g., a real-time assay) or in a set of isolated volumes (e.g., a digital assay). To perform a digital amplification assay, the sample can be distributed to isolated volumes each containing reagents to support amplification of the target sequence to form an amplicon, such as by the polymerase chain reaction (PCR). Only a subset of the isolated volumes receive at least one copy of the target sequence. The volumes may be subjected to conditions, such as thermal cycling, that promote amplification of the target sequence to an endpoint. A signal may be detected from the volumes after the endpoint has been reached. The signal may indicate which of the volumes contain the amplicon and thus received at least one copy of the target sequence when the volumes were formed. The concentration of target sequence may be calculated by Poisson statistics using the number of volumes that are positive (or that are negative) for the amplicon, and a total number of volumes.

Amplification assays for target sequences containing a repetitive sequence of a microsatellite can be problematic. These assays can suffer from inefficient target sequence amplification, low signal, and/or high background. Moreover, a normal allele of the target sequence containing the entire repetitive sequence may not be distinguishable from mutant alleles of the target sequence missing nucleotides from the repetitive sequence. There is a need for new amplification assays to detect mutant alleles that alter a repetitive sequence.

SUMMARY

The present disclosure provides methods and compositions for detecting genetic instability using digital amplification assays. The methods may be performed in a set of isolated volumes and generally may involve competitive hybridization of a competitor and a probe/primer with a normal allele and one or more mutant alleles of a microsatellite locus. The competitor may be configured to compete similarly with, or to outcompete, the primer/probe for hybridization with the normal allele. The primer/probe may be configured to outcompete the competitor for hybridization with various mutant alleles of the locus that alter the length of the repetitive sequence by different amounts. Isolated volumes in which the primer/probe outcompetes the competitor may be enumerated, and represent one or more of the mutant alleles. The methods may enable diagnosing microsatellite instability and treating a subject based on the diagnosis.

DETAILED DESCRIPTION

Figure 1:
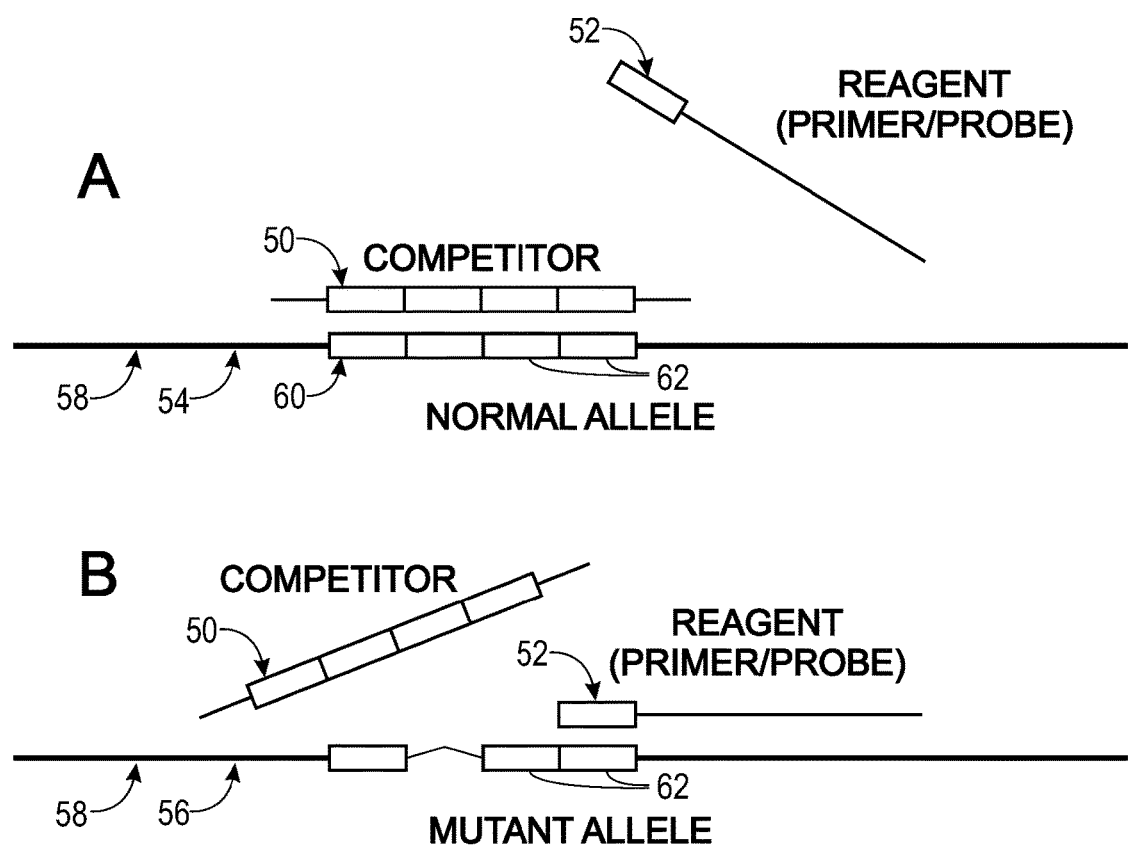
FIG. 1 is a schematic representation of competition that can occur in each of the assay configurations disclosed herein, namely, competitive hybridization of a competitor and a reagent (a primer/probe) to a normal allele and a mutant allele of a microsatellite locus.

The present disclosure provides methods and compositions for detecting genetic instability using digital amplification assays. The methods may be performed in a set of isolated volumes and generally may involve competitive hybridization of a competitor and a probe/primer with a normal allele and one or more mutant alleles of a microsatellite locus. The competitor may be configured to compete similarly with, or to outcompete, the primer/probe for hybridization with the normal allele. The primer/probe may be configured to outcompete the competitor for hybridization with various mutant alleles of the locus that alter the length of the repetitive sequence by different amounts (i.e., when different numbers of nucleotides are missing from the repetitive sequence). Isolated volumes in which the primer/probe outcompetes the competitor may be enumerated, and represent one or more of the mutant alleles. The methods may enable diagnosing microsatellite instability and treating a subject based on the diagnosis.

An exemplary method of detecting mutant alleles is provided. The mutant alleles may alter (e.g., delete at least part of) a repetitive sequence present in a normal allele of a microsatellite locus. In the method, a set of isolated volumes may be formed. Each volume may include (i) a primer pair including a forward primer and a reverse primer configured to amplify a target region of the locus, (ii) a label, and a (iii) competitor. Each volume of only a subset of the volumes may contain the target region from the normal allele. Each volume of a plurality of the volumes may not contain the target region from any of the mutant alleles. The competitor may be configured to compete at a similar efficiency with, or outcompete, a reagent present in the volumes for hybridization with the normal allele. The reagent may be configured to outcompete the competitor for hybridization with each of the mutant alleles. The competitor, relative to the reagent, may base-pair with more nucleotides of the repetitive sequence when hybridized with the normal allele. The reagent may be the forward primer and/or a strand of a probe, where the probe includes the label. Amplicon may be generated using the primer pair. Amplification data may be collected from the label, which reports generation of the amplicon.

Another exemplary method of detecting mutant alleles is provided. The mutant alleles may alter a repetitive sequence present in a normal allele of a microsatellite locus. In the method, a set of isolated volumes may be formed. Each isolated volume may contain (i) a primer pair including a forward primer and a reverse primer configured to amplify the normal allele and each of the mutant alleles, (ii) a first probe having a label, and (iii) a second probe having a label. Each volume of only a subset of the volumes may contain the normal allele. Each volume of a plurality of the volumes may contain none of the mutant alleles. Amplicon may be generated using the primer pair. Amplification data may be collected from the label of each probe. The strand of the first probe and the strand of the second probe may competitively hybridize at a similar efficiency with amplicon corresponding to the normal allele. The strand of the second probe may be configured to outcompete the strand of the first probe for hybridization with amplicon corresponding to each of the mutant alleles. A strand of the first probe, relative to a strand of the second probe, may base-pair with more nucleotides of the repetitive sequence when hybridized with the normal allele.

The sensitivity of assays disclosed herein can be tuned, in part, by the design of the assay components, such as the sequences of the competitor and the reagent (primer/probe) that compete with one another. For example, the amount of overlap of the sequences of each of the competitor and the reagent with the repetitive sequence helps to determine which deletion alleles of the repetitive sequence are detectable as different from the normal allele. (The amount of overlap can be defined as the number of nucleotides matching, or base-pairs formed with, the repetitive sequence.) The number of different detectable deletion alleles may be directly related to the amount of overlap of the competitor with the repetitive sequence (i.e., the number and the amount increase or decrease together). The number of different detectable deletion alleles may be inversely related to the amount of overlap of the reagent with the repetitive sequence. Accordingly, if the respective melting temperatures of the competitor and reagent hybridized with the normal allele are held constant during design of these components, the most deletion alleles (i.e., the largest range of deletion sizes) may be detectable when (a) the competitor overlaps the entire repetitive sequence and (b) the reagent binds to a flanking sequence near the repetitive sequence but overlaps none of the repetitive sequence. Stated another way, the difference in amount of overlap for the competitor relative to the reagent is directly related to the number of deletion alleles that are detectable.

The sensitivity of assays disclosed herein also can be tuned, during assay design, based on the chosen difference in melting temperature, if any, between the competitor and the reagent for hybridization with the normal allele. The melting temperature of the competitor may be greater than that of the reagent (such as at least about 2, 3, 4, or 5 degrees greater), such that the competitor outcompetes the reagent for hybridization with the normal allele. As this difference in melting temperature is decreased, the assay becomes more sensitive to smaller deletions within the repetitive sequence. The greatest sensitivity may be achieved when the respective melting temperatures are substantially the same, such as less than about one degree different from one another.

The assays disclosed herein permit detection of mutant alleles having a range of sizes of deletions in the repetitive sequence of a locus. The range of detectable sizes (i.e., the difference in size between the largest and smallest detectable deletions) may be at least 5, 6, 8, 10, 12, 15 or more nucleotides. The smallest detectable deletion may be 1, 2, 3, 4, or 5 nucleotides, among others. The largest detectable deletion is generally the difference in amount of overlap of the competitor and the reagent with the repetitive sequence, minus the size of the smallest detectable deletion. For example, if the repetitive sequence is 20 nucleotides in length, the competitor overlaps all 20 nucleotides, the reagent overlaps none of the 20 nucleotides, and the sensitivity of detection is a deletion of two or more nucleotides, then the range in sizes of mutants that are detectable is 18 nucleotides.

The present disclosure describes use of dual-strand probes to improve assay performance. In PCR reactions where endpoint detection is used for quantification of a target, dual-strand probes allow for better discrimination between amplification-positive and amplification-negative fluid volumes. This better discrimination may be beneficial for low-efficiency PCR reactions, such as for mutant alleles involving a repetitive sequence.

Designing a digital amplification assay that involves a repetitive sequence of low complexity, such as a mononucleotide or dinucleotide repeat sequence, is challenging and often not possible with standard assay design rules. This may be due to a change in the on- and off-rates of low-complexity primers and/or probes. Whatever the cause, the result is generally poor signal discrimination between amplification-positive and amplification-negative volumes.

The assay configurations disclosed herein offer various advantages including better signal discrimination between amplification-positive and amplification-negative volumes, lower background, and tunable sensitivity to changes in the repetitive sequence. Moreover, the assay configurations may permit a range of different-length deletions of the repetitive sequence to be detected with equal efficiency. Accordingly, genetic instability, if any, of a microsatellite locus can be detected in a sample with higher sensitivity, more rapidly, more robustly, with a sample of lower quality/purity, and/or in more types of samples. Moreover, microsatellite instability associated with the sample can be diagnosed without electrophoresis or sequencing, as used in the prior art. The assays disclosed herein may enable the genetic instability of a plurality of different microsatellite loci to be tested efficiently, robustly, and with high sensitivity using the assay configurations disclosed herein, to evaluate microsatellite instability of a sample. The level of mutant alleles detected for each of the loci may be used to assess whether the sample indicates impaired DNA mismatch repair (MMR) (producing microsatellite instability) in a subject providing the sample, particularly in a cancer-associated sample collected from the subject.

Further aspects of the present disclosure are presented in the following sections: (I) definitions, (II) assay configurations, (III) assay, diagnostic, and treatment methods, (IV) compositions, and (V) examples.

I. DEFINITIONS

Technical terms used in this disclosure have the meanings that are commonly recognized by those skilled in the art. However, the following terms may have additional meanings, as described below.

Allele—one of the alternative forms of a nucleotide sequence or gene at a specific chromosomal location (locus) or present in a target region therein. A "normal" allele is a wild-type allele, the most prevalent allele or pair of alleles in the sample, and/or the allele(s) inherited from progenitors. A "mutant" allele is an altered form of the normal allele created by deletion of one or more nucleotides, insertion of one or more nucleotides, a change in the identity of one or more nucleotides, and/or rearrangement of the normal allele.

Amplicon—the product(s) of an amplification reaction. An amplicon may be generated by amplification of a target region. The amplicon may be described as amplified target region, although the sequence of the amplicon, particularly at primer binding sites, may not exactly match that of the target region.

Amplification—a process whereby multiple copies are made of an amplicon from a target region. Amplification may generate an exponential or linear increase in the number of copies as amplification proceeds. Typical amplifications may produce a greater than 1,000-fold increase in copy number. Exemplary amplification reactions for the assays disclosed herein may include the polymerase chain reaction (PCR), which is driven by thermal cycling. The assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable amplification reagents incorporated into a set of isolated volumes. The reagents may include any combination of at least one primer pair, at least one probe including a label, a competitor, an intercalating dye, at least one polymerase enzyme (which may be heat-stable), and nucleoside triphosphates (dNTPs and/or NTPs), among others.

Checkpoint protein—a protein that helps keep immune responses in check and can prevent T cells from killing cancer cells. Checkpoint proteins are made by some types of immune system cells, such as T cells, and some cancer cells. Exemplary checkpoint proteins include adenosine A2A receptor (A2AR), B7-H3/CD276, B7-H4/VTCN1, B and T lymphocyte attenuator (BTLA, also called CD272), cytotoxic T-lymphocyte-associated protein 4 (CTLA-4), indoleamine 2,3-dioxygenase (IDO), killer-cell immunoglobulin-like receptor (KIR), lymphocyte activation gene 3 (LAG-3), programmed death-1 receptor (PD-1), T-cell immunoglobulin domain and mucin domain 3 (TIM-3), and V-domain Ig suppressor of T cell activation (VISTA).

Checkpoint inhibitor—a drug that binds to and blocks a checkpoint protein or a ligand thereof. Checkpoint inhibitors can be used to treat cancer (e.g., carcinomas, sarcomas, melanomas, lymphomas, and leukemias), and may be more effective when the cancer exhibits a high level of microsatellite instability. Exemplary checkpoint inhibitors that block PD-1 include pembrolizumab (Keytruda®), nivolumab (Opdivo®), pidilizumab, AMP-224, AMP-514, PDR001, and cemiplimab. PD-L1 (programmed death ligand-1) can, for example, be blocked with atezolizumab (Tecentriq®), avelumab (Bavencio®), or durvalumab (Imfinzi®). LAG-3 can, for example, be targeted with BMS-986016, and IDO with apacadostat (INCB24360) or navoximod (GDC-0919). CTLA-4 can, for example, be blocked with ipilimumab (Yervoy®).

Competitor—a reagent that competes with a primer and/or a strand of a probe for annealing to a target region, an amplicon, a normal allele of a locus, and/or mutant alleles of the locus. The competitive annealing may occur during and/or after amplification. The competitor may include an oligonucleotide, and may be a blocker, a strand of a probe, and/or a primer, among others. The competitor may form base pairs (e.g., successive base pairs without mismatch) with at least 50%, 75%, 90% or all of the nucleotides constituting a strand of the repetitive sequence of the normal allele. The competitor also may base-pair with one or more nucleotides flanking the repetitive sequence at only one end or at both ends of the repetitive sequence.

Droplet—a small amount of liquid encapsulated by an immiscible fluid (e.g., a carrier liquid, such as a continuous phase of an emulsion). Isolated volumes for the assays herein may, for example, have an average size of less than about 500 nL, 100 nL, 10 nL, or 1 nL.

Hybridize—form a double-stranded nucleic acid by base-pairing between a pair of separate strands. Also called annealing. The double-stranded nucleic acid may include mismatches and/or one or more single-stranded regions.

Isolated volumes—discrete amounts of fluid that are separate from one another. The volumes may be separated from one another by gas (e.g., air), liquid (e.g., an immiscible carrier liquid or continuous phase), a solid (e.g., a wall(s) of a sample holder (such as a multi-well sample holder)), or a combination thereof, among others. The volumes may be substantially the same size as one another. Exemplary volumes are droplets surrounded by a continuous carrier liquid, such as aqueous droplets encapsulated by a continuous oil phase, which may form an emulsion. The volumes may have substantially the same composition, except for stochastic variations in limiting components (e.g., target regions and/or alleles) supplied by a sample. The volumes may be aliquots (interchangeably called partitions) of the same mixture.

Label—an identifying and/or distinguishing marker or identifier associated with a structure, such as a primer, probe, competitor, amplicon, isolated volume, or the like. The label may be associated covalently with the structure, such as a label that is covalently attached to an oligonucleotide, or associated non-covalently (e.g., by intercalation, hydrogen bonding, electrostatic interaction, encapsulation, etc.). Exemplary labels include optical labels, radioactive labels, magnetic labels, epitopes, enzymes, antibodies, etc. Optical labels are detectable optically via their interaction with light. Exemplary optical labels that may be suitable include photoluminophores, quenchers, and intercalating dyes, among others.

Locus—a specific chromosomal location. Based on how the locus is defined, any suitable length of nucleotide sequence may be present at a locus, such as less than about 1000, 500, or 200 nucleotides, among others.

Melting temperature (Tm)—the temperature at which one-half of a double-stranded nucleic acid (or a "duplex") is dissociated into a pair of independent strands, and indicates the stability of the duplex. The melting temperature may be determined in part by the length, nucleotide content, and degree of perfect complementary of the base-pairing sequences of the pair of strands. The concentration of each strand, the ionic strength of the solution, and the concentration of a chemical denaturant (e.g., formamide), if any, in the solution also may affect the melting temperature.

A pair of duplexes may be formed with one another in the same isolated volume by competitive hybridization of two different strands with respective overlapping sequences of the same partner strand. The duplexes have substantially the same melting temperature if neither is predominant.

Microsatellite instability (MSI)—a form of genetic instability in which the repetitive sequence of a microsatellite locus exhibits a change(s) in length from the normal allele of the locus, typically by deletion (or insertion) of one or more nucleotides from the repetitive sequence. The instability may be global or localized in a subject. Localized instability may occur in certain tissues (e.g., cancerous tissues) or cells (e.g., cancerous cells) of the subject. MSI can be observed by comparing the allele(s) present at a microsatellite locus in healthy (normal) and cancerous tissue. MSI is manifested as the presence (e.g., above a predetermined frequency) of one or more mutant alleles having a deletion (or insertion) of one or more repeat units at the repetitive sequence of the microsatellite locus. This form of instability indicates that cells in a subject are error-prone when replicating, recombining, and/or repairing DNA.

Microsatellite locus—a region of genomic DNA that includes a repetitive sequence. The region may be defined to contain the repetitive sequence and a flanking sequence at one or both ends of the repetitive sequence, for the normal allele of the locus. The boundaries of a microsatellite locus can be defined arbitrarily. Microsatellite loci can be very sensitive indicators of genetic instability. The mutation rate of low-complexity repetitive sequences within these loci may be orders of magnitude greater than high-complexity sequences of the same length, particularly when the DNA mismatch repair (MMR) system is not functioning properly. This mutation rate may increase with decreasing complexity of repetitive sequences, with mononucleotide or dinucleotide repeat units generally being the most sensitive indicators of MSI.

MSI-H—a term used to classify a sample (e.g., a cancer-associated sample) as having a high frequency of MSI. If five microsatellite loci are analyzed, the sample is classified as MSI-H when at least two of the loci show instability. When more than five microsatellite loci are analyzed, the sample is classified as MSI-H when at least 30% of the microsatellite loci are found to be unstable.

MSI-L—a term used to classify a sample (e.g., a cancer-associated sample) as having a low, but detectable, frequency of MSI. If five microsatellite loci are analyzed, the sample is classified as MSI-L when only one of the loci shows instability. When more than five microsatellite loci are analyzed, the sample is classified as MSI-L when at least one but less than 30% of the microsatellite loci are found to be unstable.

MSS—a term referring to a sample (e.g., a cancer-associated sample) that is microsatellite stable, when no microsatellite loci tested exhibit instability. The distinction between MSI-L and MSS may only be established more reliably when a significantly greater number of loci than five are tested.

Nucleic acid—a substance comprising a strand of nucleotide monomers or an analog thereof. A nucleic acid may be single-stranded or double-stranded (i.e., base-paired with another nucleic acid strand), among others. Each strand of a nucleic acid may be composed of any suitable number of monomers, such as at least about ten or one-hundred, among others. Generally, the length of a nucleic acid strand corresponds to its source, with synthetic nucleic acids (e.g., oligonucleotides) typically being shorter, and biologically/ enzymatically generated nucleic acids (e.g., genomic fragments) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (G)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone and/or to one or more nucleobases. Exemplary artificial nucleic acids include glycol nucleic acids (GNA), peptide nucleic acids (PNA), locked nucleic acids (LNA), threose nucleic acids (TNA), and the like.

The sequence of a nucleic acid strand is defined by the order in which nucleobases are arranged along the backbone. This sequence generally determines the ability of the nucleic acid strand to hybridize with a partner strand by hydrogen bonding. In particular, adenine pairs with thymine (or uracil) and guanine pairs with cytosine. A nucleic acid strand that can hybridize with another nucleic acid strand in an antiparallel fashion by forming a consecutive or nearly consecutive string of base pairs is termed "complementary."

Oligonucleotide—a relatively short nucleic acid. An oligonucleotide may, for example, be synthesized chemically or produced by fragmenting a larger polynucleotide. Exemplary oligonucleotides are less than about 200, 100, or 50 nucleotides in length. The oligonucleotide may include a backbone and/or nucleobases that are not naturally occurring in DNA or RNA.

Partial occupancy—not present in every volume of a set of isolated volumes. Each allele and/or corresponding target region may have a random distribution among the volumes of a set, and a low concentration, such that each volume of only a subset of the volumes contains at least one copy of the allele and/or target region. For example, only of subset of the volumes may contain a normal allele of a locus, and only a subset of the volumes may contain any one of the detectable mutant alleles of the locus. Stated another way, a plurality of the volumes may not contain the normal allele, and/or a plurality of the volumes may contain none of the detectable mutant alleles of the locus.

PCR—nucleic acid amplification that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. PCR generally produces an exponential increase in the amount of amplicon over successive cycles.

Photoluminescence—emission of light produced by absorption of photons. Photoluminescence may be light emitted in response to irradiation with excitation light, and includes fluorescence, phosphorescence, etc. A "photoluminophore" is an atom, functional group, moiety, or compound capable of photoluminescence, and may be a fluorophore and/or a phosphor, among others. Suitable photoluminophores may include a photoluminescent moiety such as FAM™, VIC®, HEX™, ROX™, TAMRA™, JOE™, Cy™3, Cy™5, or the like. Light includes ultraviolet light, visible light, and infrared light.

Primer—an oligonucleotide that hybridizes with a strand of a template in such a manner that the 3' terminus of the oligonucleotide can act as a site of polymerization (primer extension) using a polymerase enzyme. Exemplary primers are synthesized chemically. Primers may be supplied as a primer pair for amplification of a target region. The primers of the primer pair may hybridize with opposite strands of the target region and/or amplicon corresponding thereto. The primers of the primer pair can be called a forward primer and a reverse primer, although these are arbitrary designations. The primer pair defines the boundaries (and thus generally the size) of the target region and resulting amplicon.

Probe—a nucleic acid including at least one label and configured to report amplification via the at least one label. The nucleic acid generally includes a strand that is a sequence-specific binding partner for a target region and/or corresponding amplicon. A probe may have only one nucleic acid strand (a single-strand probe) or a pair of nucleic acid strands (a dual-strand probe) that are complementary to one another. Each strand may comprise a chain formed by an oligonucleotide, and at least one label that is covalently attached to the chain.

A single-strand probe may have a plurality of labels covalently attached to the chain, such as a photoluminophore and at least one quencher to quench the photoluminophore in a proximity-dependent manner. Degradation of the probe during primer extension (e.g., by polymerase-catalyzed hydrolysis) and/or a change in conformation of the probe (e.g., a molecular beacon probe) when hybridized with amplicon can reduce or eliminate quenching of the photoluminophore.

A dual-strand probe may include a first strand and a second strand each comprising at least one label. The first strand may hybridize with amplicon and the second strand, but preferentially with the amplicon. In other words, the first strand may form a duplex with the amplicon that has a higher melting temperature than a duplex created by the hybridization of the first and second strands to each other. Accordingly, the first strand may be longer than the second strand and/or may base-pair with more nucleotides of the amplicon. The melting temperature of the duplex formed with the first strand and the amplicon may be about the same as, or above, the annealing/extension temperature used for amplification. This melting temperature may, for example, be at least about 3, 5, 7, or 10 degrees Celsius above the melting temperature of the duplex created when the first and second strands hybridize with one another. The melting temperature of the duplex created with the first and second strands may be below the annealing/extension temperature (e.g., at least about 3, 5, 7, or 10 degrees Celsius below) but above the detection temperature at which photoluminescence is detected. In some embodiments, the first strand (or the second strand) may include a photoluminophore and no quencher therefor, and the second strand (or the first strand) may include one or more quenchers for the photoluminophore. In other embodiments, the first strand (or the second strand) may include a photoluminophore and at least one quencher therefor, and the second strand (or the first strand) may include one or more additional quenchers for the photoluminophore. The second strand may have its 3' end blocked (such as by phosphorylation, a quencher, or a fluorophore) to prevent extension by polymerase.

Quencher—a label capable of quenching the photoluminescence of a photoluminophore, generally in a highly proximity-dependent manner. A quencher may be another photoluminophore, or may be a dark quencher that does not substantially emit light. Exemplary dark quenchers may include Black Hole Quencher® dyes (e.g., BHQ®-0, BHQ®-1, BHQ®-2, and BHQ®-3), ATTO™ quenchers, Iowa Black® quenchers, QSY® 7/9/21/35, etc.

Quenching—a proximity-dependent process that results in a decrease in the photoluminescence intensity of a photoluminophore. The quenching may occur through any suitable mechanism or combination of mechanisms, including dynamic quenching (e.g., Förster Resonance Energy Transfer (FRET), Dexter electron transfer, Exciplex, etc.) or static/contact quenching, among others. The efficiency of quenching may be very sensitive to the distance between a photoluminophore and its quencher(s). For example, in FRET the efficiency of quenching is inversely related to this distance raised to the sixth power. Accordingly, small changes in the separation distance between the photoluminophore and quencher can produce large changes in the efficiency of quenching. The distance at which the quenching efficiency has dropped to 50% may be less than 10 nanometers.

Repetitive sequence—a tract of DNA or RNA composed of a tandem array of at least six repeat units (interchangeably termed repeats). The repeat unit can be a mononucleotide, dinucleotide, trinucleotide, tetranucleotide, or longer motif. In some embodiments, the repetitive sequence may include at least 8, 10, 12, 15, or 20 repeat units in the tandem array (e.g., to produce a mononucleotide sequence of this length). The repetitive sequence may be at least 8, 10, 12, 15, or 20 nucleotides in length. The assays disclosed herein may allow detection of a series of mutant alleles in which the number of repeat units and/or the length of the repetitive sequence is different between the normal allele and each of the mutant alleles, and also is different among the mutant alleles.

Sample—a part or amount for testing. A sample may include nucleic acid, such as DNA and/or RNA. The DNA may, for example, be genomic DNA, cDNA, extrachromosomal DNA, or the like. A portion of a sample, as used herein, constitutes any part of the sample (including the solvent), such as one or more nucleic acid molecules/fragments of the sample's nucleic acid, water molecules of the sample's solvent phase, one or more other molecules, and/or the like. The sample may be a normal or reference sample (providing a normal allele) or a test sample (to be tested for the presence of mutant alleles).

Target region—a region of a locus serving as a template for amplification with a primer pair. The boundaries of the target region may be determined by the primer pair. However, the target region may be defined as including or excluding the binding sites for the primer pair. Amplification of the target region generates amplicon corresponding to the target region. The target region in a given sample may represent a normal allele(s) and/or one or more mutant alleles. A target region may have a normal form provided by the normal allele and one or more mutant forms provided by mutant alleles, each having a different sequence. The target region may be considered to have the same terminal boundaries as the alleles, or as overlapping the alleles but having one or more different boundaries.

II. ASSAY CONFIGURATIONS

This section describes exemplary configurations of primers, probes, labels, target regions, repetitive sequences, loci, competitors, and reagents that may be utilized in any of the methods of Section III, and exemplary differences in competitor and reagent (primer/probe) annealing to mutant alleles relative to a normal allele of a locus; see FIGS. 1-14.

The figures described in this section and Section V use the following conventions. Each locus is represented by a heavier solid line, with the precise terminal boundaries of the locus being arbitrary or not shown. An optional repetitive sequence or sequence portion thereof within the locus, or within a probe or primer, is represented by at least one box or a series of boxes. Each box represents a repeat unit (e.g., a repeat unit of 1, 2, 3, 4, 5 or more nucleotides) within the repetitive sequence.

Each single-strand probe, and any separated strand of a dual-strand probe, is shown with its 5' end leftward of its 3' end unless specified otherwise. Each dual-strand probe, when shown as a duplex containing both strands, has the upper strand of the duplex in the same 5' to 3' orientation as a single-strand probe, and has the lower strand in the opposite orientation. Each label of a probe (e.g., unspecified fluorophores F, F1, and F2, specified fluorophores FAM and HEX, and unspecified quencher Q) is shown as attached to a chain of the probe using a short line segment that extends obliquely from the chain to the label. The line segment does not require or preclude any particular connecting structure between the chain and the label.

Each primer has an arrowhead at its 3' end to indicate the direction of primer extension by polymerase during amplification. Accordingly, the arrowhead is at the righthand end of each "forward" primer, and at the lefthand end of each "reverse" primer, although these designations are arbitrary and swappable. An "X" in place of an arrowhead represents a 3' end of a strand that is not extendable by polymerase. An "X" at a 5' end of a strand indicates that the strand is resistant to degradation (e.g., hydrolysis) by polymerase.

Competitor, reagent (a primer and/or a strand of a probe), and normal-allele sequences that match or are complementary to one another are vertically aligned and thus overlap horizontally. A large "X" over the central portion of a competitor or reagent, or a skewed orientation for the competitor or reagent, indicates that the competitor or reagent hybridizes inefficiently during/after amplification because the competitor or reagent, respectively, is outcompeted by the reagent or competitor.

FIG. 1 illustrates competition that can occur in each of the assay configurations disclosed herein to enable detection of mutant alleles of a locus. Each assay may be performed with isolated volumes each containing a competitor 50 and a reagent 52. Competitor 50 may be at least a strand of a probe (e.g., see FIGS. 2 and 7-9), a primer (e.g., see FIG. 9), a non-extendable oligonucleotide (e.g., see FIGS. 6, 13, and 14), a non-hydrolyzable oligonucleotide (e.g., see FIG. 6), or a combination thereof. Reagent 52 may be a primer, at least a strand of a probe, or a combination thereof.

The volumes collectively also may contain a normal allele 54 and at least one mutant allele 56 of a microsatellite locus 58. Each volume of only a subset of the volumes may contain a copy of normal allele 54, and/or each volume of only a subset of the volumes (if any) may contain a copy of mutant allele 56.

Normal allele 54 may include a repetitive sequence 60 including a tandem array of a repeat unit 62. Four repeat units 62 are shown in FIG. 1 for normal allele 54, but any suitable number of repeat units may be present in the normal allele. Repetitive sequence 60 may be altered in mutant allele 56 to change the number of repeat units present. For example, here, one repeat unit 62 has been deleted in mutant allele 56.

Competitor 50 and reagent 52 are configured to competitively hybridize with overlapping sequences of normal allele 54. The competitor and reagent can be configured to compete similarly for hybridization with normal allele 54, or can be configured such that the competitor outcompetes the reagent (as in panel A of FIG. 1). In contrast, the reagent outcompetes the competitor for hybridization with mutant allele 56 (see panel B of FIG. 1). The difference in competitive hybridization of competitor 50 and reagent 52 to normal and mutant alleles is leveraged in the assay configurations described herein to detect mutant allele 56.

The competitor may need to be relatively long if it spans the full repetitive sequence and extends beyond the repetitive sequence at both ends to base-pair with flanking nucleotides, particularly when the sequence is a mononucleotide repeat of A or T. As an example, a repetitive sequence of 27 consecutive A nucleotides may use a competitor of 45 nucleotides in order to both span the repetitive sequence, have a reasonable anneal/extend temperature, and include some specific nucleotides that base-pair outside the repetitive sequence. If the competitor is a single-strand probe including a photoluminophore and a quencher, the probe can have high background photoluminescence due to the distance between the photoluminophore and the quencher. Using a dual-strand probe instead, with the competitor being the first strand of the probe, can reduce the background significantly.

Figure 2:
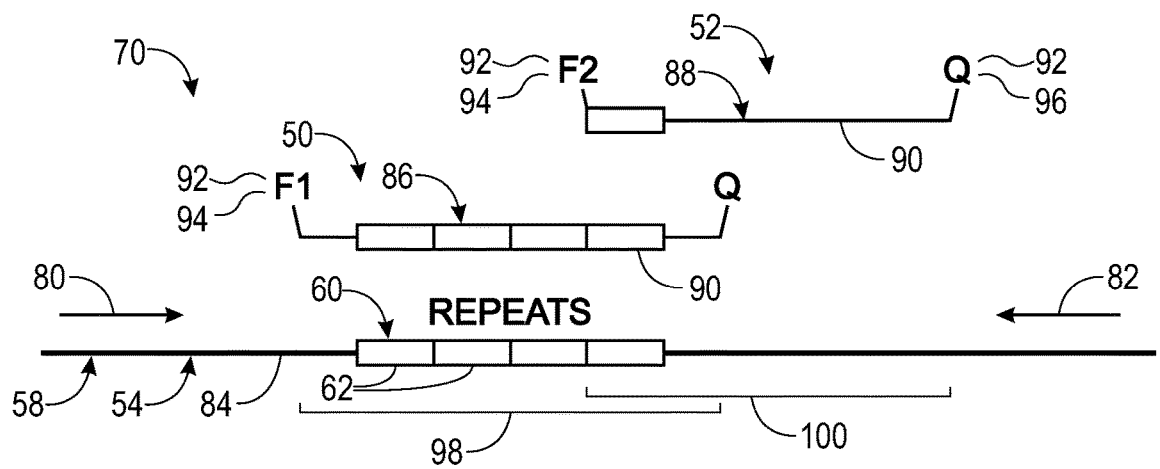
FIG. 2 is a schematic representation of an exemplary assay configuration for detecting mutant alleles that alter a repetitive sequence present in a normal allele of a locus, using a pair of probes that anneal to overlapping sequences within the normal allele.

FIG. 2 shows an exemplary assay configuration 70 for detecting mutation of a microsatellite locus 58 using isolated volumes in the methods disclosed herein. Each isolated volume, when formed, contains a pair of primers 80, 82 (i.e., a forward primer and a reverse primer) to amplify a target region 84 of locus 58. Each primer may be unlabeled, as shown here, or may include at least one label and may provide a strand of a probe (see below). Each primer may or may not overlap repetitive sequence 60. In the depicted embodiment, repetitive sequence 60 is located between respective binding sites for the primers in the locus and does not overlap either binding site. With this arrangement, the entire repetitive sequence can be deleted without affecting either primer binding site.

Each isolated volume, when formed, also contains a pair of probes 86, 88. Each probe may be a single-strand probe, as depicted here, or a dual-strand probe, as described below, among others. Each strand of the probe may have an oligonucleotide chain 90 and one or more labels 92 attached thereto, such as covalently linked to the chain. In the depicted embodiment, each probe is an optically-detectable hydrolysis probe, and contains a photoluminophore 94 (F1 or F2) and at least one corresponding quencher 96 (Q). The probes may contain structurally different labels, such as different photoluminophores 94 that emit light of different wavelengths from one another to allow the labels to be distinguished. For example, the different photoluminophores may be fluorophores, which are identified here as F1 and F2. In other embodiments, the probes may contain different amounts of the same label moiety, such as different amounts of F1 or different amounts of F2, and may be distinguishable from one another by the intensity of light emitted. Each probe may be hydrolyzed by polymerase when bound to a template during an extension phase of an amplification cycle, to separate photoluminophore 94 from at least one quencher 96 of the probe. Alternatively, each probe may be a molecular beacon probe.

Probes 86, 88 respectively correspond to competitor 50 and reagent 52 (also see FIG. 1). The probes may hybridize with partially overlapping annealing sequences 98, 100 of normal allele 54 of the locus, such that the probes compete with one another when binding to amplicon corresponding to normal allele 54. One or both probes overlap with at least part of repetitive sequence 60. "Normal" probe 86, also called a first probe, may be configured to base-pair with a larger number of nucleotides of repetitive sequence 60 than "mutant" probe 88, also called a second probe. The normal probe may anneal to at least a majority of repetitive sequence 60 by length (e.g., at least 70%, 80%, or 90% of the repetitive sequence, or all of the repetitive sequence as in the depicted embodiment). Mutant probe 88 may anneal to no more than a minority of the repetitive sequence by length (e.g., less than 30%, 20%, or 10%, or none of the repetitive sequence). This configuration makes the normal probe more sensitive to deletion of part of the repetitive sequence than the mutant probe.

Mutations affecting the repetitive sequence decrease the stability of a duplex created when normal probe 86 anneals to mutant alleles having a range of deletion sizes. In contrast, the stability of annealing of mutant probe 88 is unaffected for these mutant alleles until most (or all) of the repetitive sequence is deleted. Accordingly, normal probe 86 may be used to detect the presence of the normal allele, and mutant probe 88 may be used to detect the presence of various mutant alleles.

Figure 3:
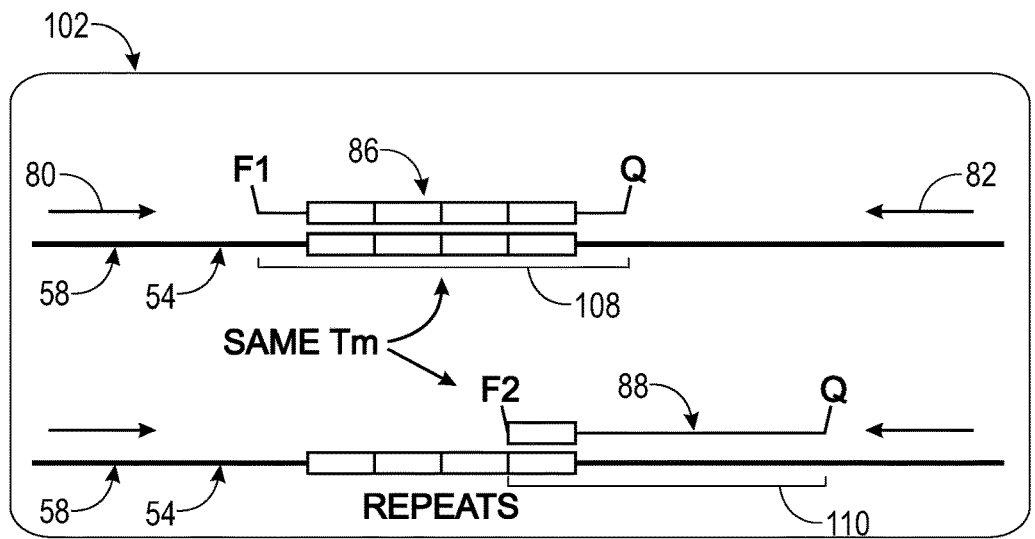
FIG. 3 is a schematic representation of a volume resulting from the assay configuration of FIG. 2, with the volume containing two copies of the normal allele of the locus, and with the pair of probes annealing to respective copies of the normal allele with similar affinity during amplification, such that the volume will be detected as amplification-positive with both probes.
Figure 4:
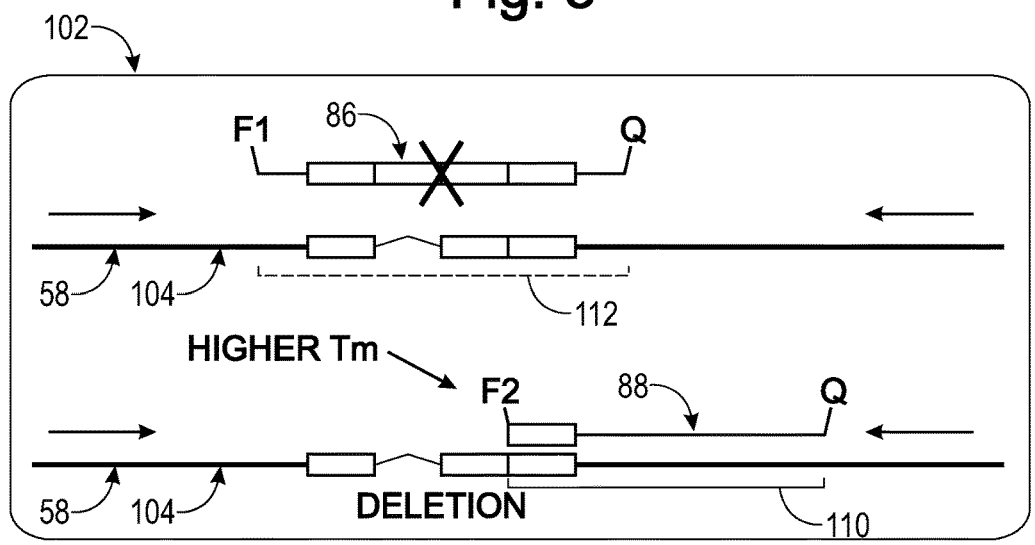
FIGS. 4 and 5 are schematic representations of different volumes resulting from the assay configuration of FIG. 2, with each volume containing two copies of a mutant allele of the locus having a deletion (FIG. 4) or an insertion (FIG. 5), and with one of the two probes outcompeting the other probe for annealing to the mutant allele during amplification as a result of the deletion or insertion, such that the volume will be detected as amplification-positive with only one of the two probes.
Figure 5:
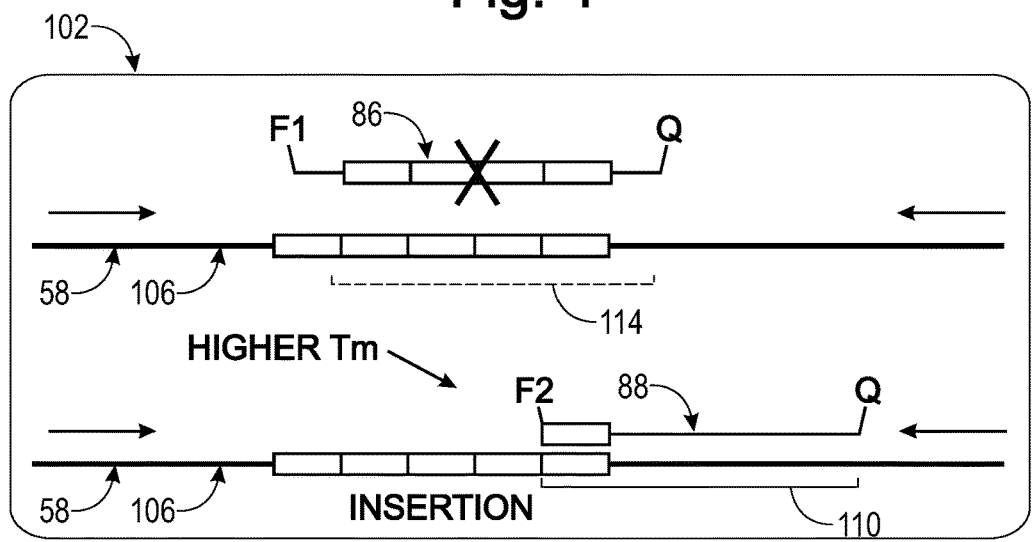

FIGS. 3-5 show isolated volumes 102 containing normal allele 54 of locus 58 (FIG. 3) and two different mutant alleles of the locus, namely, a deletion allele 104 (FIG. 4) and an insertion allele 106 (FIG. 5). Two copies of the same allele are present in each volume to permit illustrative comparison of probe melting temperatures, although the volume generally may receive only one copy of the allele when formed.

Probes 86, 88 may be configured to have any suitable melting temperatures (Tm) relative to one another when hybridized with normal allele 54 and mutant alleles 104, 106 of locus 58, and forming duplexes 108, 110, 112, and 114. The melting temperatures with normal allele 54 (duplexes 108, 110) may be substantially the same, as illustrated in FIG. 3. (For example, within two or one degree(s) of one another.) In this case, volumes containing the normal allele are amplification-positive with both probes 86, 88. Volumes containing mutant alleles 104, 106 of repetitive sequence 60 may be amplification-positive with only mutant probe 88, if the given mutant allele allows mutant probe 88 to outcompete normal probe 86 for binding to the allele, as illustrated in FIGS. 4 and 5. When the melting temperature of normal probe 86 is decreased preferentially by the mutation (outcompeted duplexes 112, 114), as shown here, the melting temperature of mutant probe 88 (duplex 110) becomes higher than that of normal probe 86 (duplex 112 or 114). In other embodiments, the melting temperature of normal probe 86 in duplex 108 may be substantially higher than that of mutant probe 88 in duplex 110, such that normal probe 86 outcompetes mutant probe 88 for binding to the normal allele. In these embodiments, volumes containing the normal allele may be amplification-positive only with normal probe 86, and volumes containing mutant alleles 104, 106 may be amplification-positive only with mutant probe 88.

Figure 6:
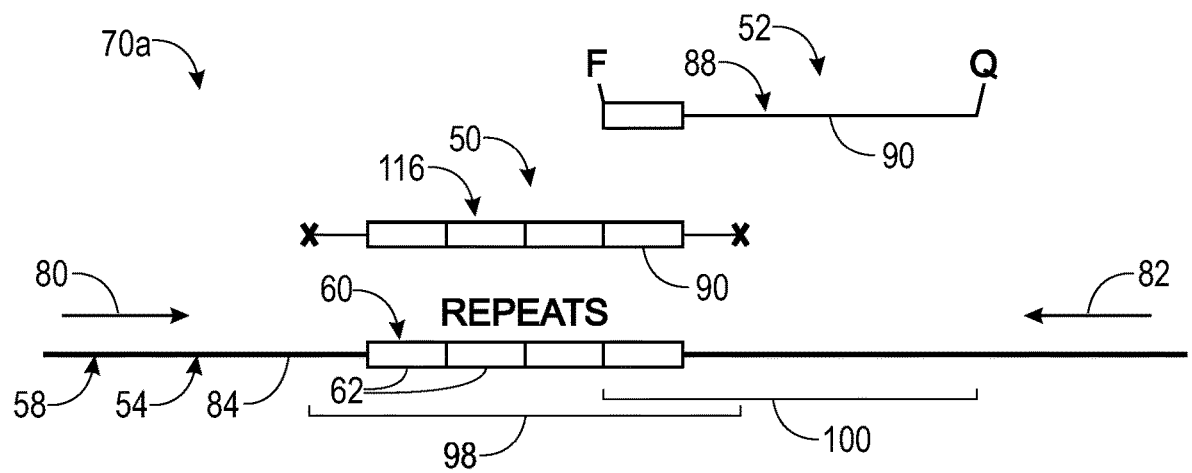
FIG. 6 is a schematic representation of an exemplary assay configuration related to the configuration of FIG. 2, except replacing one of the probes with an unlabeled competitor that outcompetes the remaining probe for hybridization to the normal allele, such that only mutant alleles are detected.

FIG. 6 shows an exemplary assay configuration 70*a* related to configuration 70 of FIG. 2. The configurations are the same except that normal probe 86 is replaced with an unlabeled competitor 116, while mutant probe 88 still corresponds to reagent 52. Chains 90 of the competitor and mutant probe 88 may have any suitable combination of features described above for the chains of normal and mutant probes 86, 88. For example, competitor 116 may be configured to outcompete mutant probe 88 for annealing to normal allele 54, but to be outcompeted by mutant probe 88 with various mutant alleles that sufficiently destabilize annealing of the competitor to these alleles. In this assay configuration, volumes that are amplification-positive with mutant probe 88 represent the mutant alleles, while volumes containing only the normal allele are amplification-negative in the collected amplification data. The assay configuration of FIG. 6 may be advantageous for a multiplex assay of different loci (e.g., different microsatellite markers) in the same set of volumes, since only one photoluminophore is used per locus.

The competitor optionally may be configured to be resistant to degradation by polymerase during amplification, such that the amount of competitor remains substantially constant and the ability to outcompete is not diminished. For example, the competitor may be a DNA/RNA analog, such as a peptide nucleic acid. Accordingly, when bound to normal allele 54, competitor 116 may block extension of forward primer 80 through the repetitive sequence. Alternatively, or in addition, competitor 116 may be modified to prevent 3' extension by polymerase.

Figure 7:
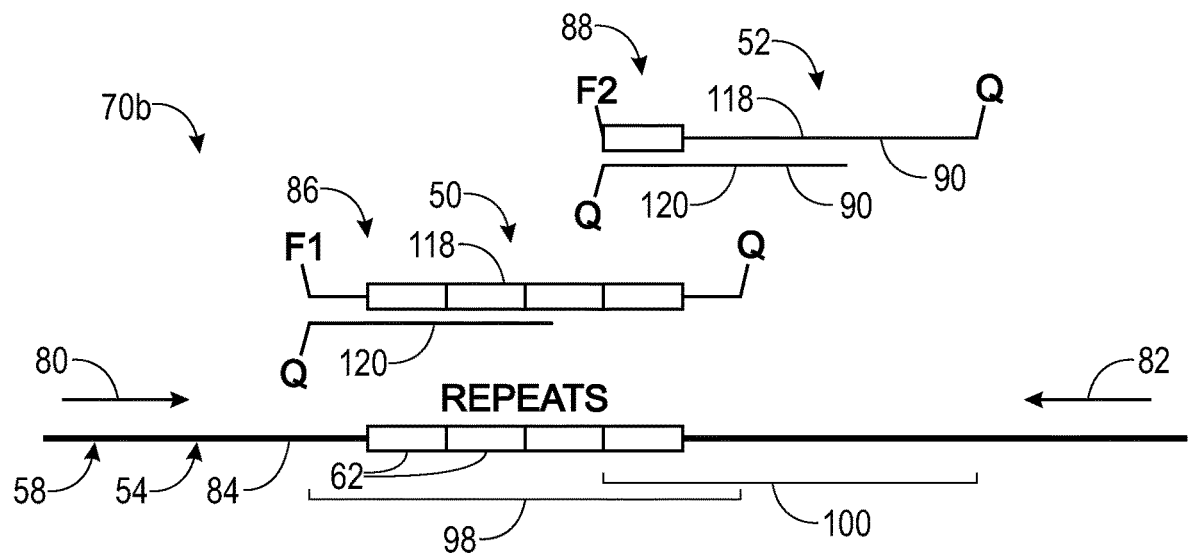
FIG. 7 is a schematic representation of another exemplary assay configuration for detecting mutant alleles that alter a repetitive sequence present in a normal allele of a locus; the assay configuration of FIG. 7 is similar to that of FIG. 2 except each of the probes is a dual-strand probe having an additional strand to decrease background when amplification data is collected.
Figure 8:
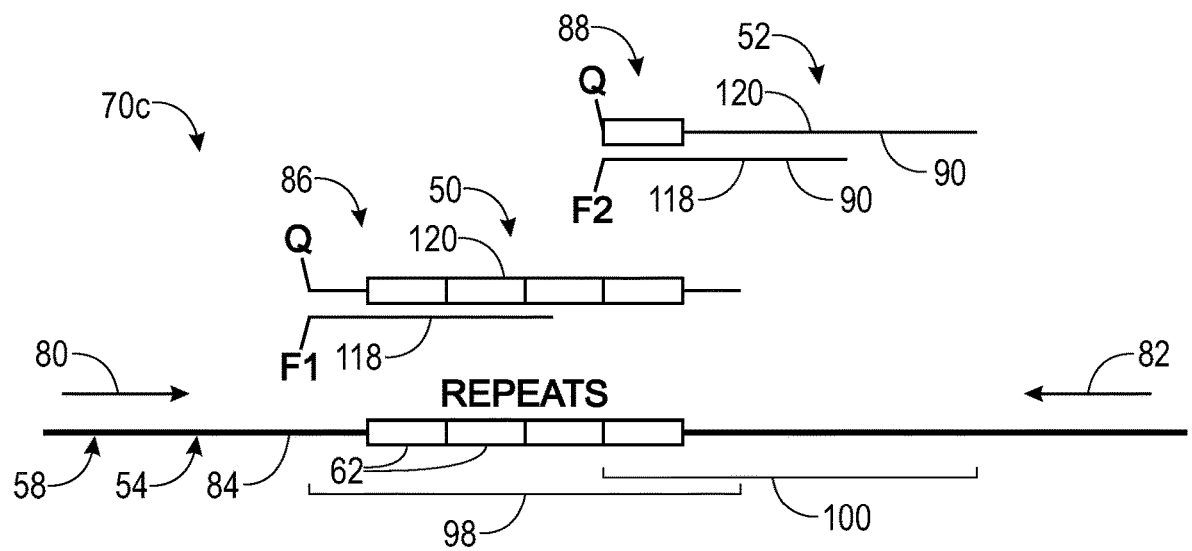
FIG. 8 is a schematic representation of still another exemplary assay configuration for detecting mutant alleles that alter a repetitive sequence present in a normal allele of a locus; the assay configuration of FIG. 8 is the same as FIG. 7 except each probe strand has only one label.

FIGS. 7 and 8 show other exemplary assay configuration 70b, 70c for detecting mutant alleles altering a repetitive sequence of a locus in the methods of Section III. Configurations 70b and 70c are the same as configuration 70 of FIG. 2, except one or both probes 86, 88 may be a dual-strand probe to reduce background. The reduced background makes amplification-positive and amplification-negative volumes more reliably distinguishable from one another with each probe. Each dual-strand probe includes a pair of labeled strands, namely, an emitter strand 118 including a photoluminophore (F1 or F2) and a quencher strand 120 including at least one quencher (Q) for the photoluminophore. Strands 118, 120 are configured to anneal with one another to form a duplex having a melting temperature above the detection temperature. (The detection temperature is the temperature at which amplification data is collected from volumes.) Once annealed, the photoluminophore (F1 or F2) is quenched by a corresponding quencher (Q) of the other strand, such as by contact quenching, and optionally also is quenched by another quencher (Q) on the same strand as the photoluminophore.

One of strands 118, 120 of each probe 86, 88 anneals more stably to normal allele 54 than to the other strand of the probe, and corresponds to competitor 50 or reagent 52. In FIG. 7, emitter strand 118 of each probe is longer than quencher strand 120 and anneals more stably to normal allele 54. In FIG. 8, quencher strand 120 of each probe is longer and anneals more stably to the normal allele. The melting temperature of the resulting duplex may be about the same as, or above, the annealing temperature and/or the extension temperature of amplification, which may allow polymerase to catalyze degradation of the annealed strand. Once degraded, the photoluminophore (F1 or F2) is no longer efficiently quenched by the quencher (Q) at the detection temperature, resulting in increased photoluminescence.

Figure 9:
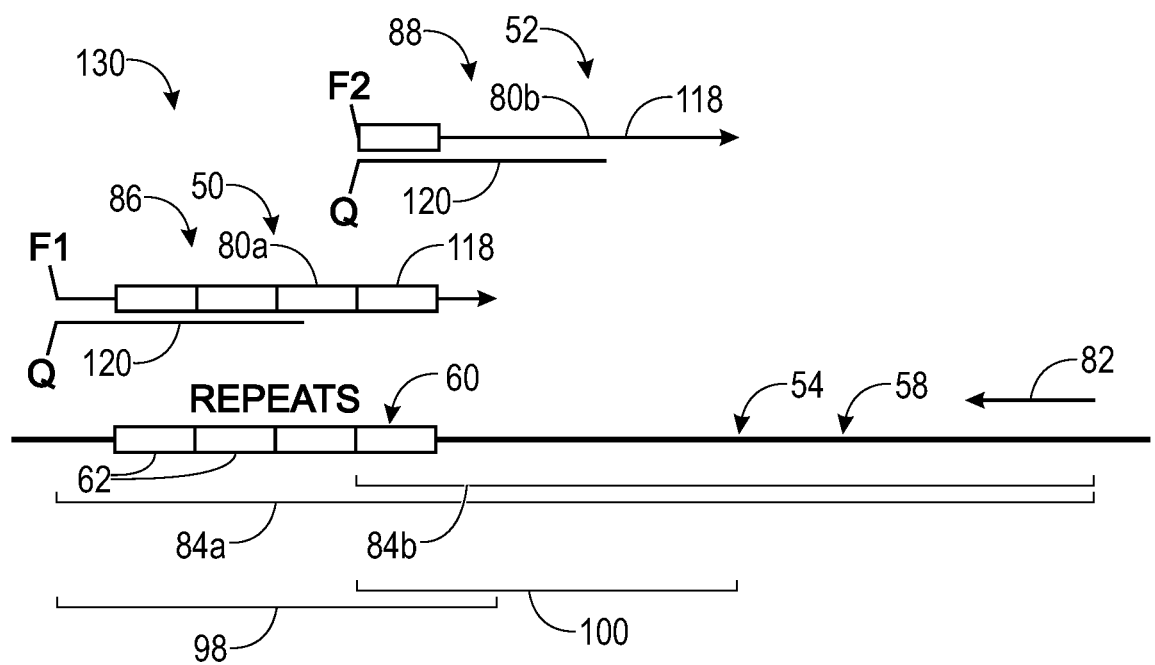
FIG. 9 is a schematic representation of yet still another exemplary assay configuration for detecting mutant alleles that alter a repetitive sequence present in a normal allele of a locus, using a pair of dual-strand probes (a "normal" probe and a "mutant" probe that anneal to overlapping sequences within a normal allele of the locus as in FIG. 7, but with one strand of each probe also being a primer for amplification.

FIG. 9 shows another exemplary assay configuration 130 for detecting mutant alleles of repetitive sequence 60 of locus 58 in the methods of Section III. Configuration 130 is related to configuration 70b of FIG. 7; both use dual-strand probes 86, 88 having respective strands that compete for hybridization with overlapping sequences 98, 100 within normal allele 54. However, configuration 130 utilizes one strand (e.g., emitter strand 118) of each probe 86, 88 as a respective forward primer 80a, 80b. Forward primer 80a correspond to competitor 50, and forward primer 80b corresponds to reagent 52. The forward primers may cooperate with the same reverse primer 82 to generate amplicon from target regions 84a, 84b. Primer 80a (e.g., emitter strand 118 of probe 86) may hybridize with a higher melting temperature to normal allele 54, such that primer 80a outcompetes primer 80b for amplification of a target region from normal allele 54. Volumes containing the normal allele are amplification-positive with probe 86. Mutant alleles that eliminate the competitive advantage of primer 80a allow primer 80b to outcompete primer 80a. Volumes containing any of these mutant alleles are amplification-positive with probe 88. Volumes containing both the normal allele and one of the mutant alleles are amplification-positive with both probes 86, 88.

Figure 10:
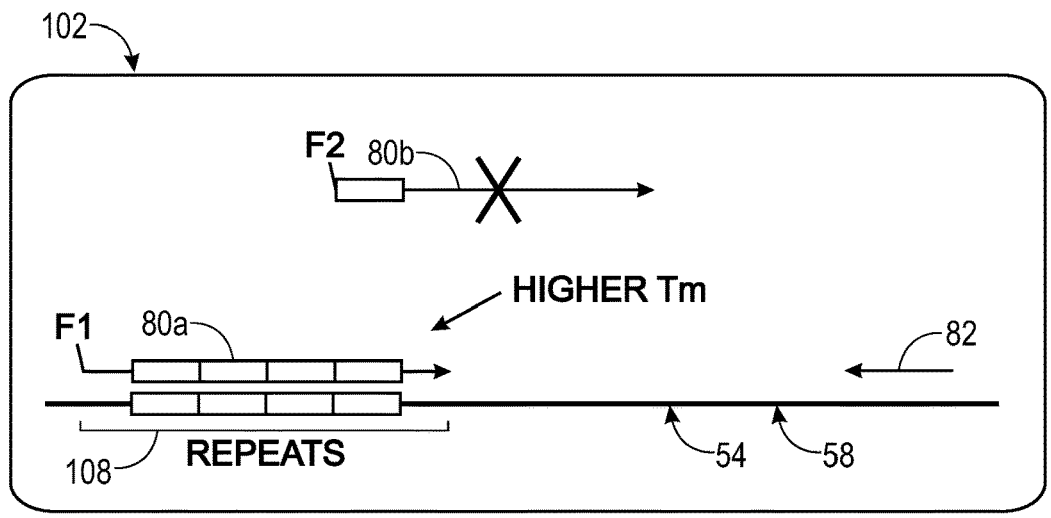
FIG. 10 is a schematic representation of a volume resulting from the assay configuration of FIG. 9, with only the primer strand of each probe shown, with the volume containing the normal allele of the locus, and with the primer strand of the normal probe outcompeting the primer strand of the mutant probe for annealing to the normal allele during amplification, such that the volume will be detected as amplification-positive with only the normal probe.
Figure 11:
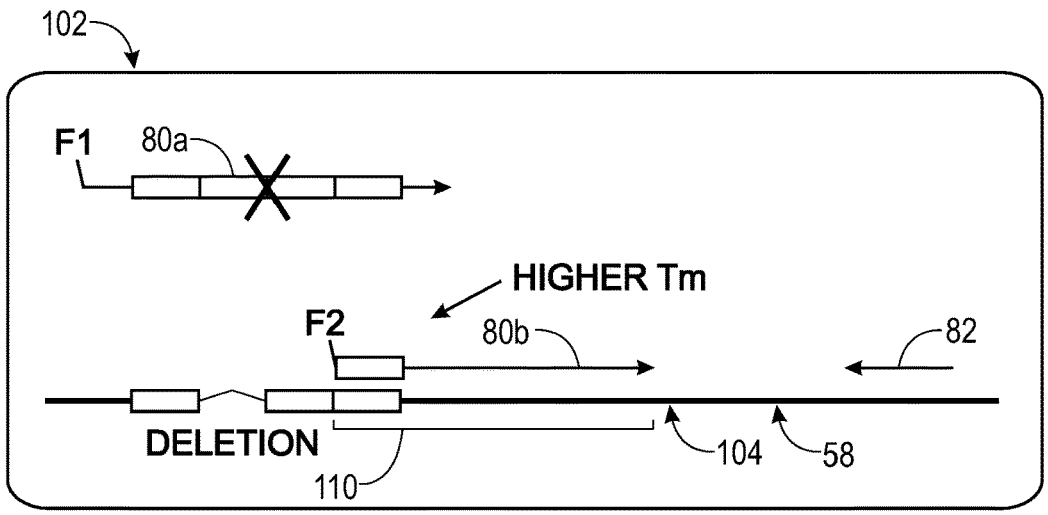
FIGS. 11 and 12 are schematic representations of different volumes resulting from the assay configuration of FIG. 9, with only the primer strand of each probe shown, with each volume containing a mutant allele of the locus having a deletion (FIG. 11) or an insertion (FIG. 12) altering the repetitive sequence, and with only the primer strand of the mutant probe annealing to the mutant allele during amplification as a result of the deletion or insertion, such that the volume will be detected as amplification-positive with only the mutant probe.
Figure 12:
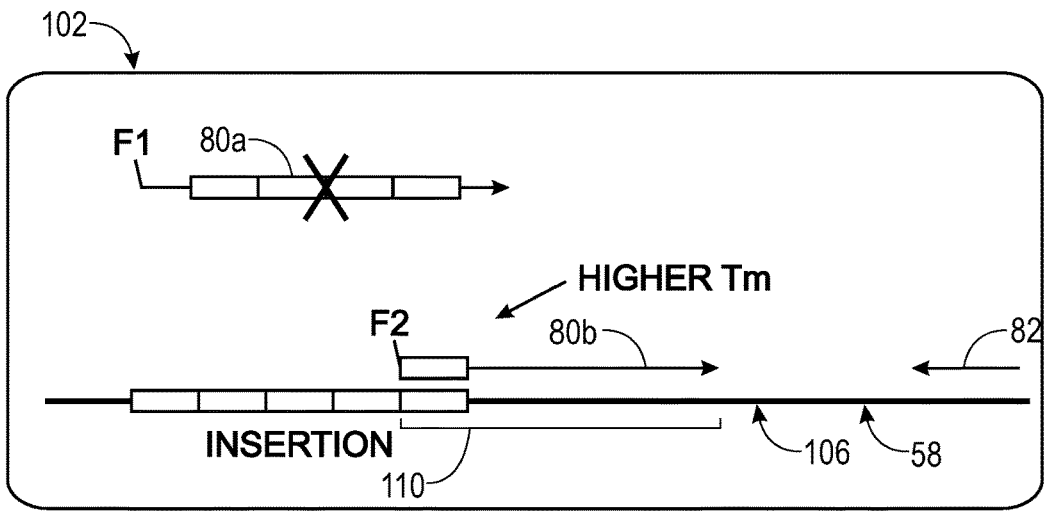

FIGS. 10-12 show volumes 102 containing normal allele 54 of locus 58 (FIG. 10), deletion allele 104 (FIG. 11), and insertion allele 106 (FIG. 12). Duplex 108 formed with annealed primer 80a and normal allele 54 has a higher melting temperature than a corresponding duplex formed with primer 80b. Accordingly, primer 80a is extended with greater efficiency than primer 80b in the presence of normal allele 54 in FIG. 10. However, duplex 110 formed with primer 80b and either mutant allele 104, 106 has a higher melting temperature than primer 80a annealed with the mutant allele (see FIGS. 11 and 12). As a result, primer 80b is extended with greater efficiency than primer 80a in the presence of only the mutant allele.

Figure 13:
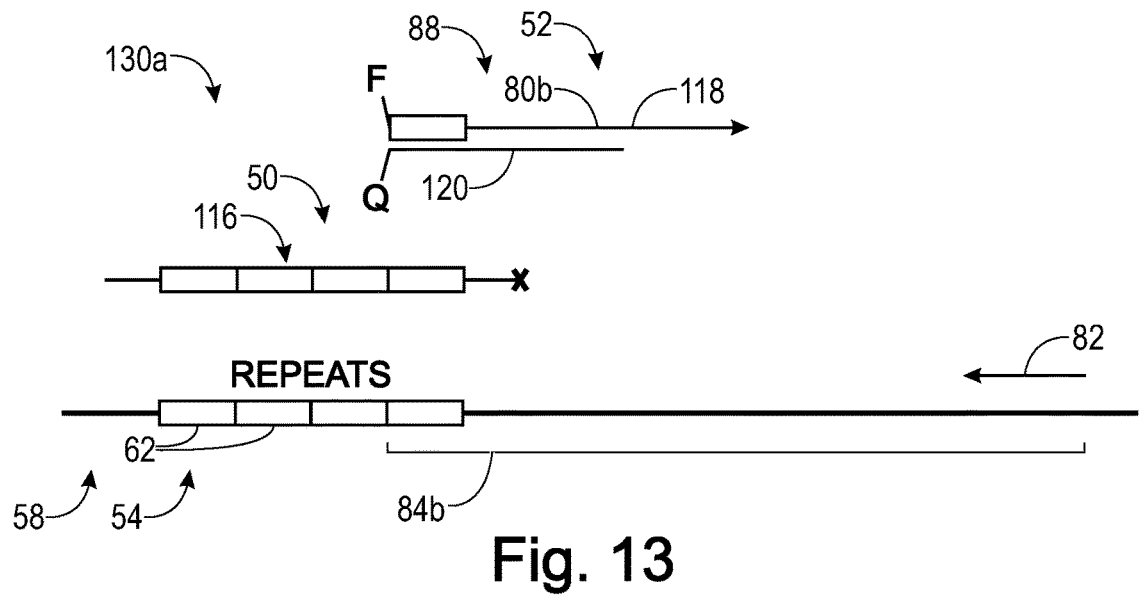
FIG. 13 is a schematic representation of an exemplary assay configuration that is similar to the configuration of FIG. 9, except replacing one of the dual-strand probes with an unlabeled, single-strand competitor.

FIG. 13 shows an assay configuration 130a that is similar to configuration 130 of FIG. 9. One difference is that normal probe 86, including primer 80a, has been replaced with an unlabeled competitor 116. The competitor may have any of the properties described above for the competitor of FIG. 6, such as a blocked 3' end, which prevents extension as a primer. Volumes containing only normal allele 54 are amplification-negative with probe 88, and volumes containing various mutant alleles (such as alleles 104, 106) are amplification-positive with the probe.

Figure 14:
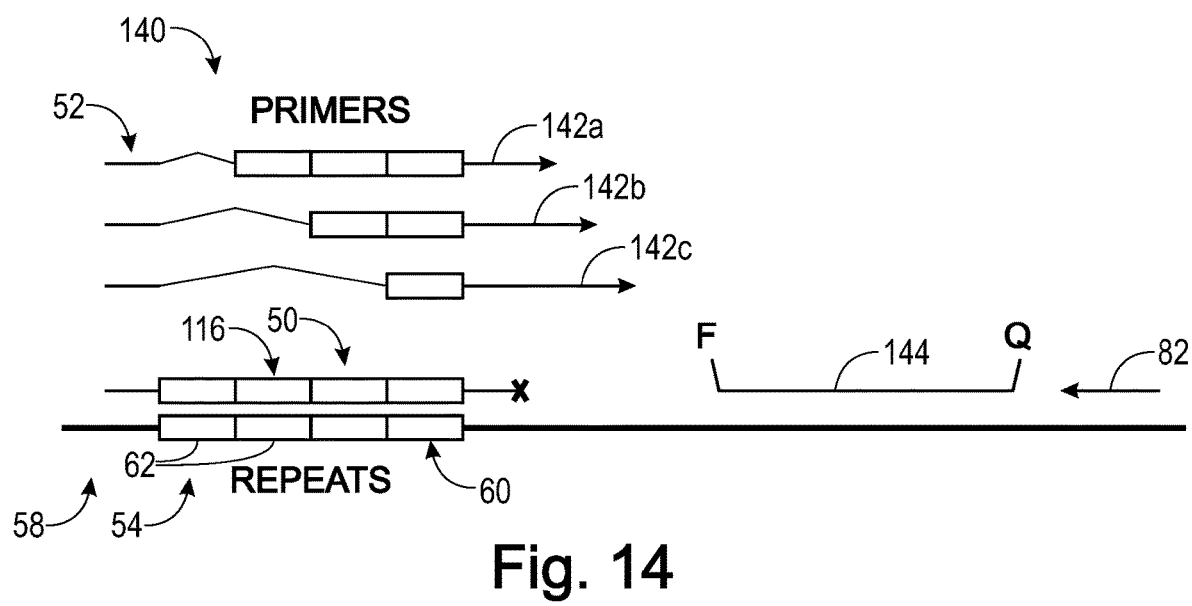
FIG. 14 is a schematic representation of still yet another exemplary assay configuration for detecting mutant alleles that alter a repetitive sequence present in a normal allele of a locus, using an amplification-blocking competitor that preferentially anneals to a normal allele to inhibit amplification thereof, and one or more primers that preferentially anneal to mutant alleles of the locus for selective amplification and detection of the mutant alleles.

FIG. 14 shows another exemplary assay configuration 140 for detecting mutant alleles altering repetitive sequence 60 of locus 58 in the methods of Section III. Configuration 140 uses an unlabeled competitor 116 as in FIG. 13, to block amplification of normal allele 54. However, labeled primer 80b is replaced with one or more unlabeled primers 142a-142c that correspond to reagent 52. The primers may be used, collectively, to amplify a series of deletion alleles of different deletion sizes. Each primer may enable detecting deletions of different sizes, if a suitable annealing temperature for amplification is selected. Accordingly, the number of different sizes of deletions detected may be greater than the number of primers 142a-c used. Volumes containing any of these detectable mutant alleles may be amplification-positive with a probe 144 or an intercalating dye. The probe may, for example, anneal intermediate forward primers 142a-c and reverse primer 82.

III. ASSAY, DIAGNOSTIC, AND TREATMENT METHODS

Figure 15:
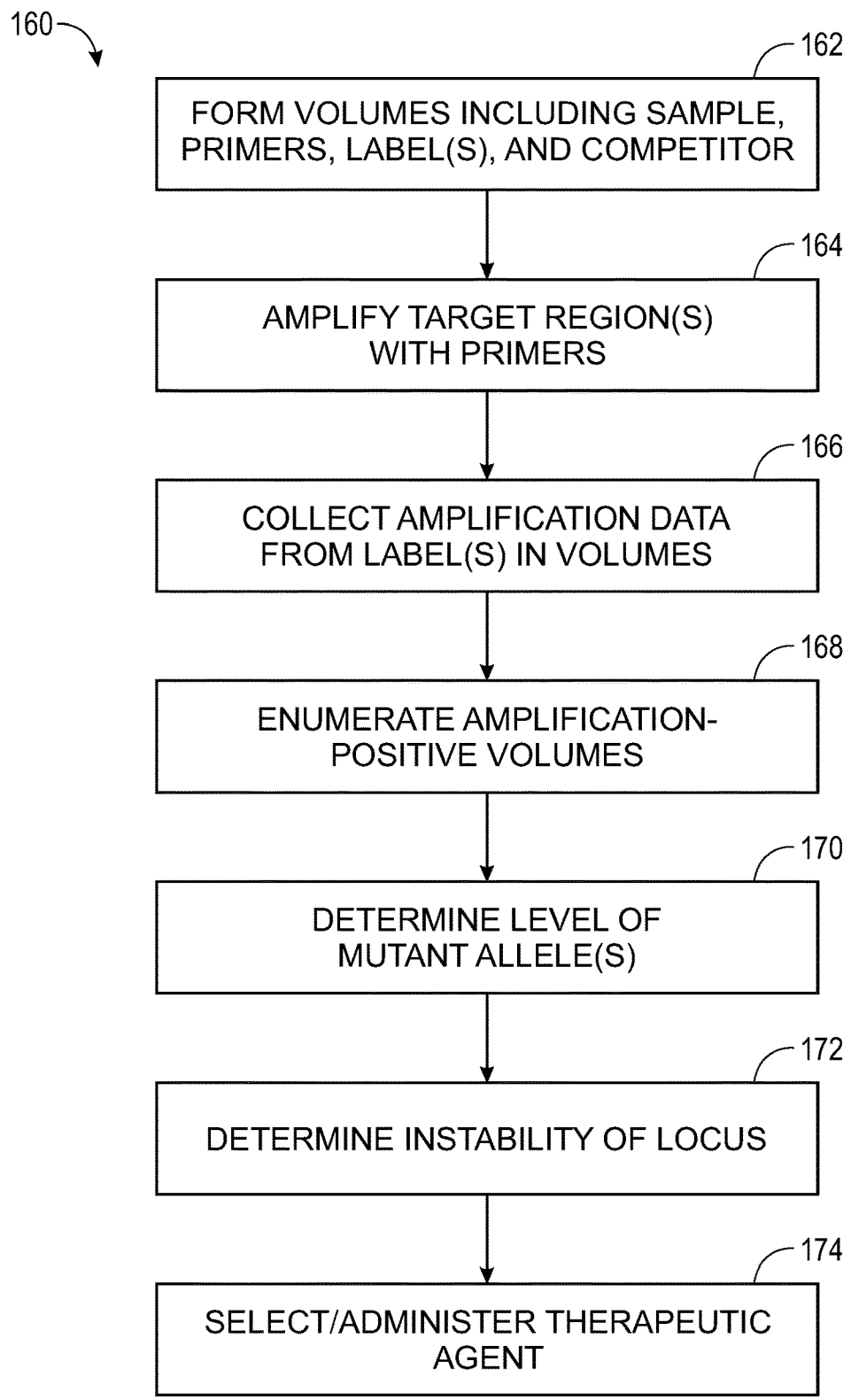
FIG. 15 is a flowchart showing exemplary steps that may be performed in a method of detecting mutant alleles of a locus, detecting genetic instability, diagnosing microsatellite instability, and/or treating cancer.

This section describes an exemplary method(s) 160 of detecting mutant alleles of each of one or more loci, determining the stability of each locus, diagnosing microsatellite instability (MSI), and/or treating a subject according to the diagnosis; see FIG. 15. The steps described in this section may be performed in any suitable order and combination, using any of the features, aspects, reagents, assay configurations, compositions, and/or approaches described elsewhere herein.

A set of isolated volumes may be formed, indicated at 162. Each volume when formed may include amplification reagents to amplify a target region(s) from at least one locus. The amplification reagents may comprise primers to amplify each target region, a label(s) that reports amplification of the target region, a competitor, nucleoside triphosphates (dNTPs/NTPs), and a polymerase. The primers for a given target region may include a primer pair (a forward primer and a reverse primer) defining the target region. The label may be provided by a single-strand or dual-strand probe, or an intercalating dye, among others. As described above in Section II, the competitor may be a primer, a strand of a single-strand or dual-strand probe, or an oligonucleotide that is non-extendable, unlabeled, and/or non-hydrolyzable in the assay.

Each volume when formed also may include a portion of the same sample, which may be provided by a subject (e.g., a human subject). The sample supplies the target region(s) from the locus (or loci). However, each portion of the sample incorporated into a respective volume does not comprise at least one copy of the target region from the normal allele (or from a mutant allele) of the locus. Accordingly, only a subset of the volumes of the set of volumes may contain the "normal" target region from the normal allele of the locus, and/or only a subset of the volumes may contain "mutant" target region from a detectable mutant allele of the locus. This "partial occupancy" of volumes by the target region allows a digital assay to be performed.

The volumes may be formed by any suitable approach. In some embodiments, the volumes may be formed by dividing a mixture into the volumes, where the mixture contains all of the amplification reagents and the sample. The mixture may be divided serially or in parallel. In other embodiments, the volumes may be formed by combining/fusing smaller volumes with one another. The step of forming volumes, and any subsequent step performed with the volumes, may create/use any suitable number of the volumes, such as at least 100, 200, 500, 1000, 2000, or 5000 volumes, among others. The volumes may be the same size to facilitate statistical analysis of amplification data. The volumes may have any suitable average size, such as less than about 1000, 100, 10, or 1 nanoliter(s).

One or more sets of volumes may be formed. Each set of volumes may be configured to detect mutant alleles of only one locus, or to distinguishably detect mutant alleles of two or more loci in a multiplex assay. The mutant alleles of each locus may be detected with a structurally-different label (e.g., from a different photoluminophore for each locus). Alternatively, the structurally-same label may be included in different probes to distinguishably detect mutant alleles of at least two different loci. For example, different amounts of the same photoluminophore may be included in the different probes to produce different changes in the detected intensity for amplification-positive volumes of the respective loci). In some embodiments, the one or more sets of volumes may be configured to detect mutant alleles of a plurality of microsatellite loci, such as at least 2, 3, 4, 5, or more microsatellite loci. For example, one set of volumes may be configured to detect mutant alleles of two microsatellite loci, and another set of volumes may be configured to detect mutant alleles of three microsatellite loci.

Each target region of a locus, if present, may be amplified in one or more volumes of a set of volumes using the primers for the target region, indicated at 164. The set of volumes may be heated and/or thermally cycled to encourage amplification, such as by PCR. In some embodiments, one target region of the locus may have the same sequence for a normal allele and mutant alleles, such that the primers for the target region would amplify the target region with substantially equivalent efficiency from each type of allele in the absence of the competitor (e.g., see primers 80b, 82 and target region 84b of FIG. 9). However, the competitor may preferentially suppress amplification of copies of the target region provided by the normal allele relative to those provide by the mutant alleles. In other embodiments, one target region may have different sequences for a normal allele (the "normal target region") and mutant alleles (the "mutant target region"). The competitor may preferentially suppress binding of a probe to amplicon from the normal target region relative to amplicon from the mutant target region, even though the binding site for the probe in each type of amplicon may be the same. Binding of the probe may be suppressed during amplification (e.g., if a strand of the probe binds to amplicon during amplification and is extended or hydrolyzed by polymerase), or after amplification has been completed (e.g., if the probe is a molecular beacon probe). If a dual-strand probe is present, amplification may be performed with an annealing temperature that is greater than the melting temperature of the dual-strand probe, such that the probe remains substantially denatured until after amplification has been completed.

Amplification data may be collected from one or more labels present in the set of volumes, indicated at 166. A property of the label may be detected and a signal corresponding to the property may be created, which are described herein as signal detection. For example, photoluminescence may be detected from each volume. The photoluminescence may be detected at a different wavelength from a label of each probe or at the same wavelength. Any suitable property of the photoluminescence may be detected, including intensity, polarization, lifetime, or a combination thereof, among others, to create a signal.

Each volume may be assigned as amplification-positive or amplification-negative for one or more target regions and/or with one or more probes using the amplification data. The signal detected from each volume, and from a given label and/or probe, may be compared to at least one threshold, to determine whether the volume is indicated to be amplification-positive or amplification-negative by the label and/or probe for a given target region. For example, the intensity detected from the volume may be compared to an intensity threshold, to determine whether the volume exhibits an intensity change characteristic of amplification-positive volumes.

Volumes indicated to be amplification-positive with one or more labels and/or one or more probes may be enumerated, indicated at 168, to obtain a value (i.e., a number of volumes). The value may represent the number of volumes that are amplification-positive with one label and/or probe, or the number of volumes that are amplification-positive with only one of two labels and/or only one of two probes. The value may represent volumes containing a detectable mutant allele of the locus. The value may be a first value. Step 168 also may include a step of enumerating volumes that are amplification-negative with the label and/or probe, and/or with each label and/or probe of two labels/probes, to obtain a second value. The second value may represent volumes that do not contain a detectable mutant allele, may represent volumes that do not contain the normal allele, or may represent volumes that contain neither the normal allele nor a detectable mutant allele. Step 168 further may include a step of enumerating volumes that are amplification-positive with a different label and/or probe, or with both of the two labels/probes, to obtain a third value. The third value may at least predominantly represent volumes containing the normal allele of the locus, and/or may more accurately represent volumes containing the normal allele of the locus and not a detectable mutant allele of the locus.

A level of detectable mutant alleles of the locus may be determined, indicated at 170. The level may be determined using any of the values enumerated in step 168. The level may be a concentration (e.g., average copy number per droplet) calculated using Poisson statistics, or the first value may be used directly. Any of the following equations may be used to determine the concentration of detectable mutant alleles and the concentration of the normal allele.

The concentration of the normal allele or detectable mutant allele (i.e., detectable mutant alleles considered collectively) may be calculated by assuming that copies of the allele or corresponding target region, before amplification, have a Poisson distribution among the volumes. With this assumption, the fraction f(k) of volumes having k copies of the allele is given by the following equation:

$$f(k) = \frac{\lambda^k}{k!} e^{-\lambda} \quad (1)$$

Here, $\lambda$ is the concentration of the type of allele (normal or detectable mutant) in the volumes, expressed as the average number of copies per volume (before amplification). Simplified Poisson equations may be derived from the more general equation above and used to determine allele concentration from either the number of volumes (i.e., the volume count) positive for the allele or the number of volumes negative for the allele, and a total number of volumes (whether positive or negative for the allele). An exemplary Poisson equation that may be used is as follows:

$$\lambda = -\ln\left(1 - \frac{N_+}{N_{tot}}\right) \quad (2)$$

where $\lambda$ is the allele concentration, $N_+$ is the number of volumes positive for the allele, and $N_{tot}$ is the total number of volumes (positive or negative for the allele). $N_{tot}$ is equal to a sum of (a) $N_+$ for the allele and (b) the number of volumes negative for the allele, or $N_-$. Another exemplary Poisson equation that may be used is as follows:

$$\lambda = -\ln\left(\frac{N_-}{N_{tot}}\right) \quad (3)$$

where $\lambda$, $N_-$, and $N_{tot}$ are as defined above.

Equations 2 and 3 above can be rearranged to produce the following:

$$\lambda = \ln(N_{tot}) - \ln(N_{tot} - N_+) \quad (4)$$

$$\lambda = \ln(N_{tot}) - \ln(N_-) \quad (5)$$

The concentration of each type of allele in an assay can, for example, be determined with any of Equations 2 to 5, using values (i.e., volume counts) obtained for $N_{tot}$ and $N_+$ (or, equivalently, $N_-$) for the allele. In some cases, the value used for $N_{tot}$ (the total volume count) may be the same for each allele. In other cases, the value used for $N_{tot}$ may vary, such as one of the populations of volumes is excluded from the total count to eliminate a mixed population. In some embodiments, $N_{tot}$ may be equivalent to a combination of all populations, namely, a sum of the volume counts for all populations identified.

The level of mutant allele (or normal allele) may be relative or absolute. For example, the level may be expressed as a ratio, which may be obtained by comparing a value representing the mutant allele (e.g., a number of mutant-containing volumes or a concentration of the mutant allele) with a corresponding value representing the normal allele (or both types of allele).

The instability, if any, of the locus may be determined, indicated at 172, based on the level of detectable mutant allele determined in step 170. This instability may be characterized by a binary designation (either stable or unstable), or as a degree of instability. The level of mutant allele may be compared with one or more threshold values to determine the instability. The threshold value(s) may be predetermined. In some embodiments, the level of mutant allele, and, optionally, the level of the normal allele, may be determined for each of two samples, which may be a normal sample and a test sample (e.g., a tumor sample) from the same or different subjects. Levels of mutant allele may be compared between the samples as part of step 172.

The instability, if any, of each of a plurality of microsatellite loci may be determined in step 172 for the same sample (and/or the same subject), and from one set of volumes, or two or more sets of volumes. The presence or degree of microsatellite instability may be determined based on the instabilities of the microsatellite loci. The determination of microsatellite instability may be based on the number of loci that are unstable, optionally out of the total number of loci tested. For example, the sample or subject may be diagnosed as having a high level of microsatellite instability (MSI-H), a lower level of microsatellite instability (MSI-L), or as microsatellite stable (MMC), as defined in Section I.

A therapeutic agent may be selected and administered, indicated at 174, based on the microsatellite instability determined in step 172. The agent may be an immunotherapeutic agent, namely, a checkpoint inhibitor (see Section I).

IV. COMPOSITIONS

Compositions for performing the assays disclosed herein are provided. Each composition may include an isolated volume. The isolated volume may comprise only one copy of a target region from a normal allele or a mutant allele of a microsatellite locus. The volume also may include a primer pair (a forward primer and a reverse primer) to amplify the target region, a label to report amplification of the target region, and a competitor. The competitor may be configured to compete similarly with, or to outcompete, a reagent in the volume for hybridization with overlapping sequences of the normal allele, if present in the volume. The reagent is the forward primer and/or a strand of a probe that includes the label. The reagent may be configured to outcompete the competitor for hybridization with any one of a series of mutant alleles, if present in the volume. The competitor, relative to the reagent, base-pairs with more of the repetitive sequence of the normal allele by length.

In some embodiments, the isolated volume is a droplet, and the composition is an emulsion including a plurality of droplets encapsulated by a carrier liquid. The droplets may be aqueous droplets, and the carrier liquid may be a continuous phase that is immiscible with each of the droplets. The carrier liquid may comprise oil. Each of the droplets may contain the primer pair, the label, the competitor, and the reagent, and only a subset of the droplets may contain the normal allele and/or only a subset of the droplets may contain a detectable mutant allele.

V. EXAMPLES

Further aspects of the present disclosure related to digital amplification assays for repetitive sequences, detecting mutant alleles, detecting genetic instability, diagnosing microsatellite instability, and treating cancer are described in the following examples. These examples are intended for illustration only and should not limit the overall scope of the present disclosure.

Example 1. Illustrative Sequences for Digital Assay Configurations

Figure 16:
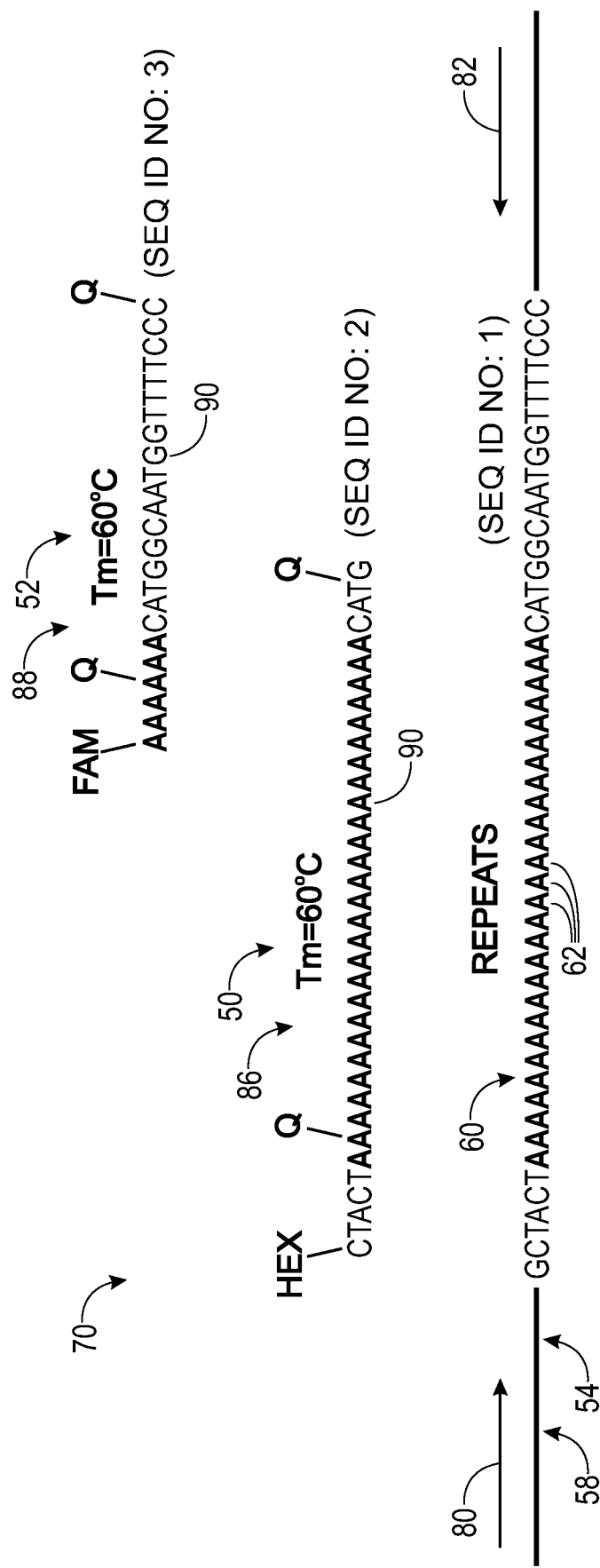
FIG. 16 is an embodiment of the assay configuration of FIG. 2 including exemplary repetitive and probe sequences that are defined.
Figure 17:
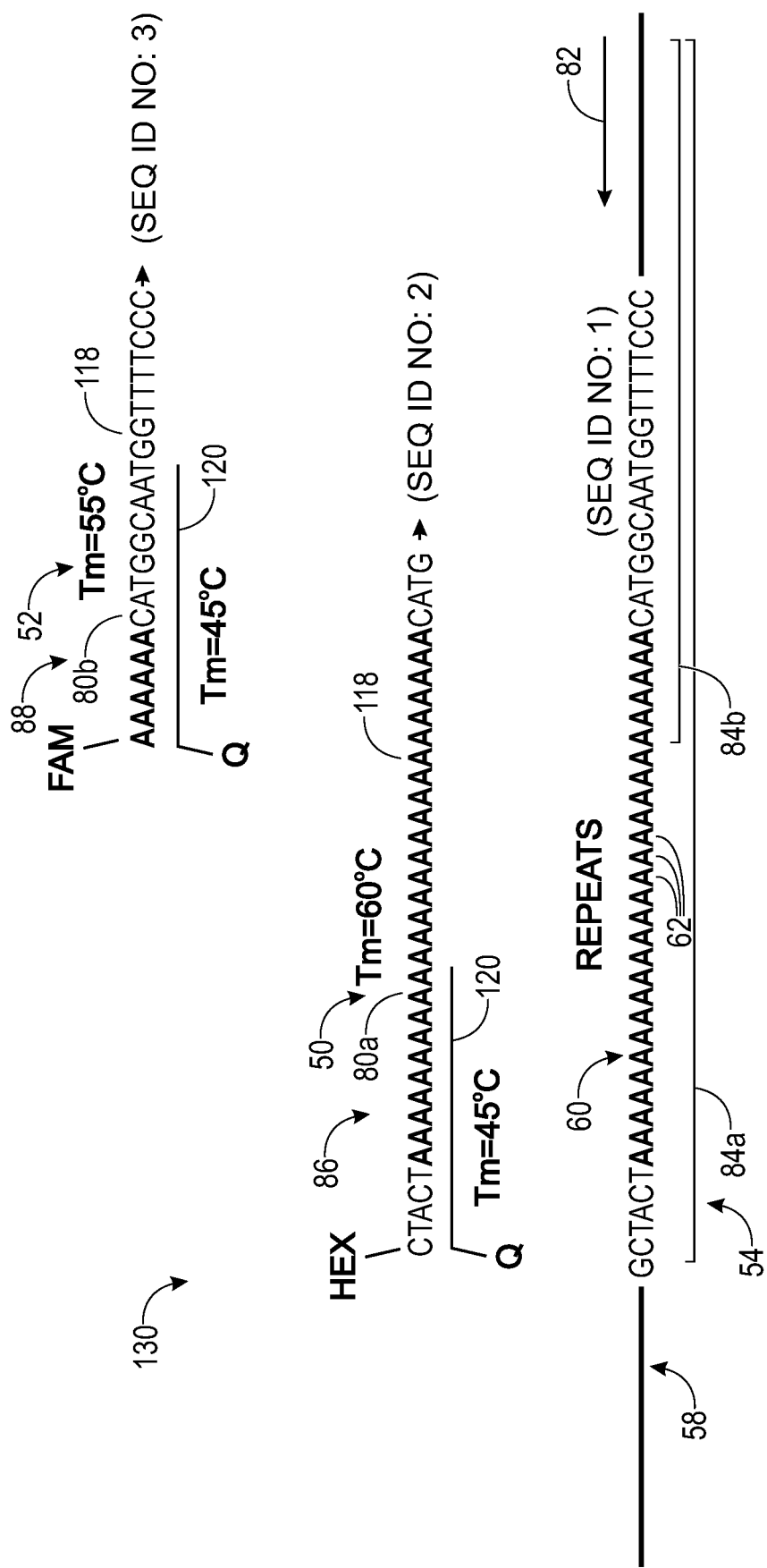
FIG. 17 is an embodiment of the assay configuration of FIG. 9 including exemplary repetitive and primer/probe sequences that are defined.
Figure 18:
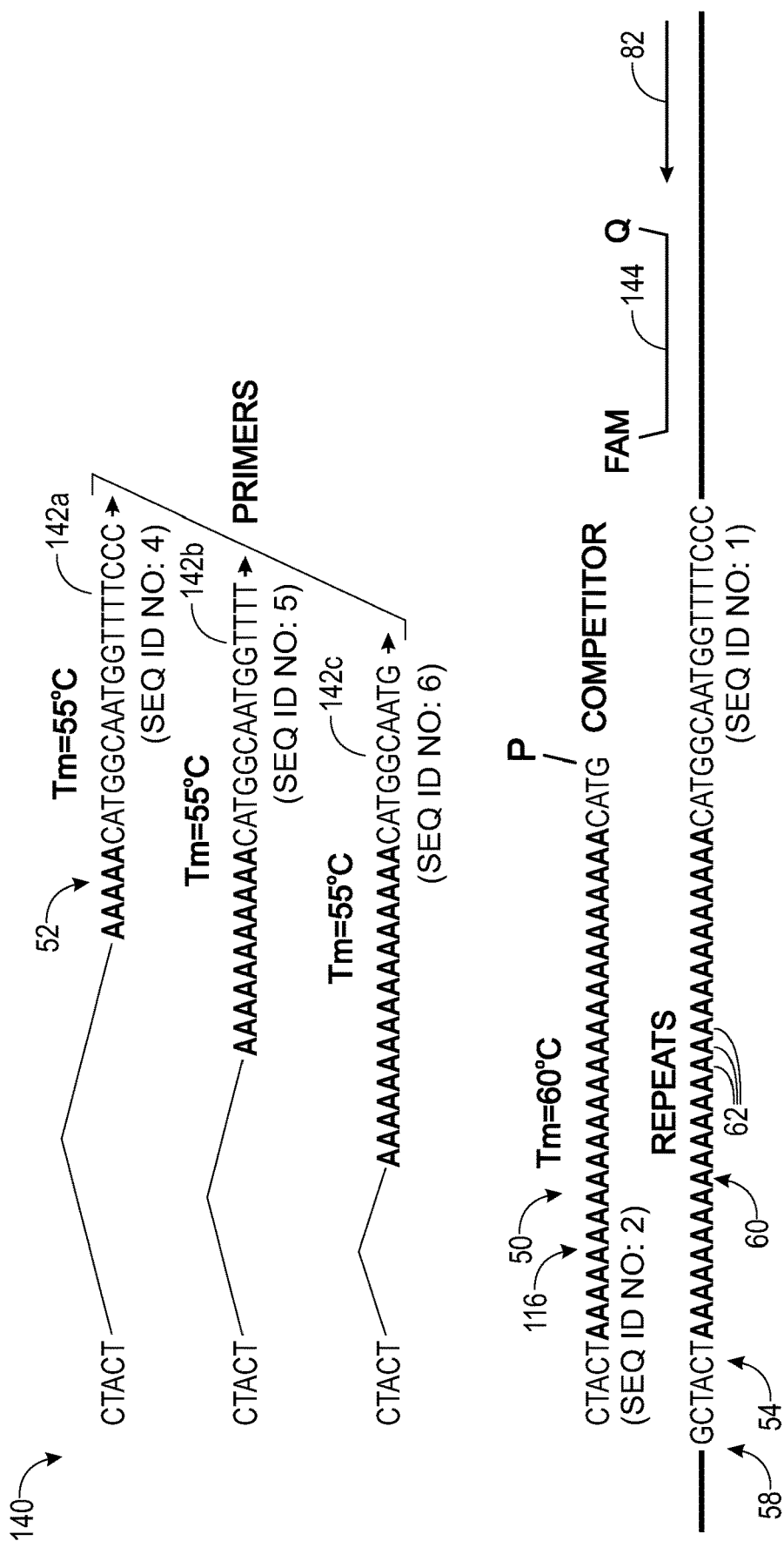
FIG. 18 is an embodiment of the assay configuration of FIG. 14 including exemplary competitor and primer sequences that are defined.

This example describes specific illustrative sequences that may be present in primers, probes, competitors, and a normal allele of an imaginary microsatellite locus in the assay configurations of FIGS. 2, 9, and 14; see FIGS. 16-18.

FIG. 16 presents an example of assay configuration 70 of FIG. 2, which utilizes probe competition. The figure shows a sequence (SEQ ID NO:1) within one of the strands of the normal allele 54 of microsatellite locus 58. The normal allele has a repetitive sequence 60 of twenty-seven adenosine (A) mononucleotides. Sequences of the respective strands for a normal probe 86 (SEQ ID NO:2) (competitor 50) and a mutant probe 88 (SEQ ID NO:3) (reagent 52) are given above normal allele 54. Positions of covalent attachment of photoluminophore labels (HEX™ and FAM™) and quencher labels (Q) to an oligonucleotide chain 90 of each probe strand are indicated. Calculated melting temperatures (Tm=60° C.) for hybridization of each probe 86, 88 with normal allele 54 are given. The melting temperatures are about the same, which allows the probes to compete with similar efficiency for hybridization with the normal allele.

FIG. 17 presents an example of assay configuration 130 of FIG. 9, which utilizes primer competition. The sequence of normal allele 54 of microsatellite locus 58 is the same as in FIG. 16, to facilitate comparison of the configurations. Sequences of respective emitter strands 118 of probe 86 (SEQ ID NO:2) and probe 88 (SEQ ID NO:3) are given. Emitter strands 118 also function as respective forward primers 80a (competitor 50) and 80b (reagent 52) for amplification of target regions 84a, 84b with the same reverse primer 82. Positions of covalent attachment of photoluminophore labels (HEX™ and FAM™) and quencher labels (Q) to strands 118, 120 are shown. Calculated melting temperatures for competitive hybridization of emitter strands 118 of probe 86 (primer 80a) and probe 88 (primer 80b) with normal allele 54 are given. The melting temperature of primer 80a (Tm=60° C.) is significantly greater than that of primer 80b (Tm=55° C.), which allows primer 80a to outcompete primer 80b for hybridization with the normal allele.

Each of probes 86, 88 in FIG. 17 is a dual-strand probe including an emitter strand 118 and a quencher strand 120. The emitter strands hybridize more stably with normal allele 54 (Tm=60° C. or 55° C.) than with quencher strand 120 (Tm=45° C.).

FIG. 18 presents an example of assay configuration 140 of FIG. 14, which utilizes primer competition. The sequence of normal allele 54 of microsatellite locus 58 is the same as in FIGS. 16 and 17, to facilitate comparison of the configurations. Sequences of non-extendable competitor 116 (SEQ ID NO:2) and forward primers 142a-c (SEQ ID NOS:4-6) are given. Competitor 116 has a 3'-phosphate (P) that blocks extension by polymerase during amplification. Calculated melting temperatures for competitive hybridization of competitor 116 (Tm=60° C.) and primers 142a-c (Tm=55° C.) with normal allele 54 are given. The melting temperature of the competitor is significantly greater than that of each forward primer 142a-c, which allows the competitor to outcompete each primer 142a-c for hybridization with the normal allele.

Example 2. Amplification Data for BAT26 Microsatellite Instability

Figure 19:
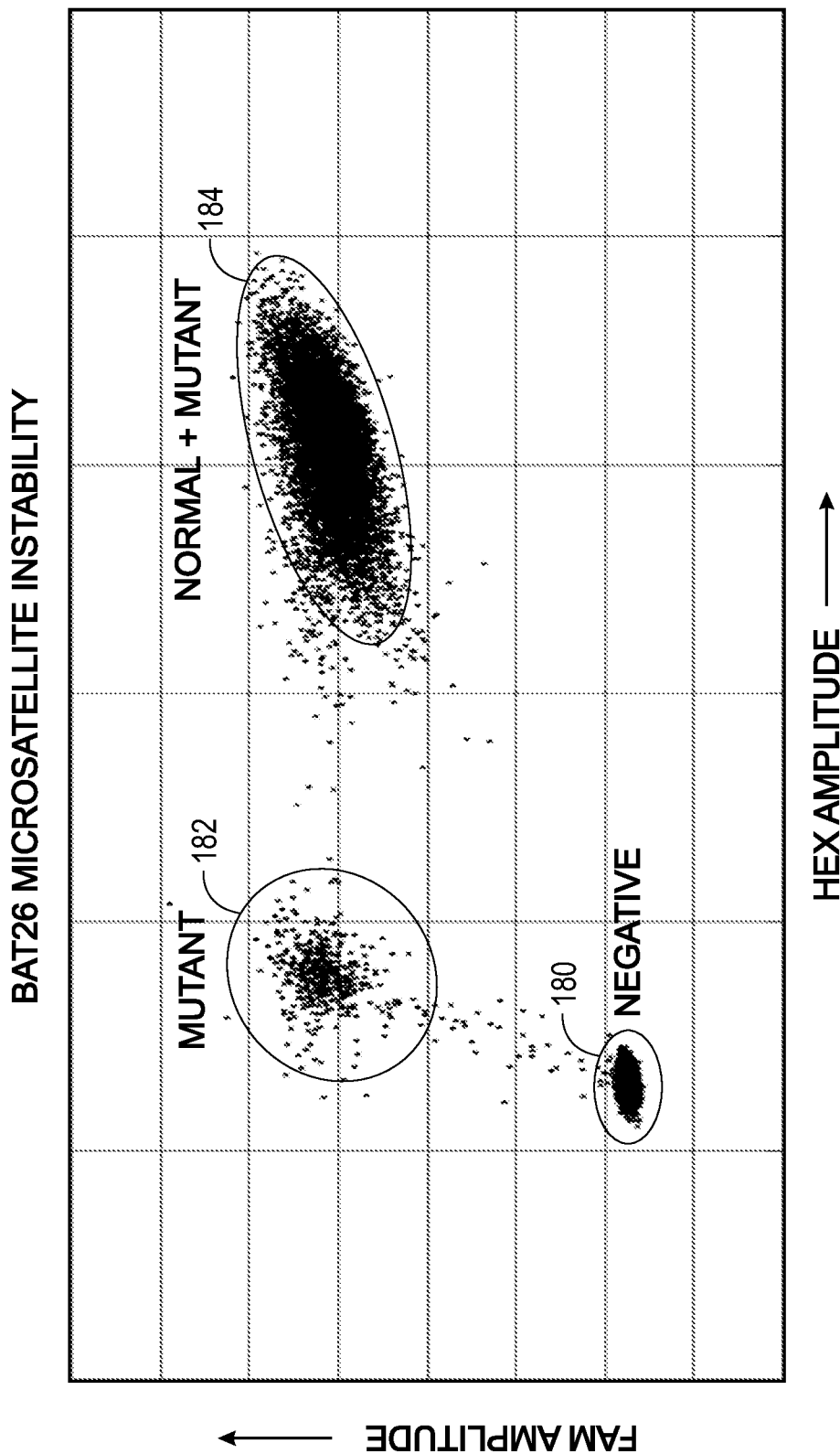
FIG. 19 is a scatter plot of photoluminescence intensity data collected after PCR amplification of a target region from a BAT26 microsatellite locus in droplets containing primers and probes for the BAT26 locus according to the assay configuration of FIG. 2.

This example presents amplification data collected in a digital amplification assay conducted according to the assay configuration of FIG. 2; see FIG. 19.

The figure shows a scatter plot of photoluminescence intensity data collected from droplets after PCR amplification of a target region from the BAT26 microsatellite locus. PCR amplification was performed in the droplets in the presence of probes 86, 88 (also see FIG. 2). Each point (dot) in the plot represents a single droplet. Normal probe 86 is labeled with HEX™ and mutant probe 88 with FAM™ (as in FIG. 16). Clusters of points representing different populations 180, 182, 184 of droplets are identified. The "negative" droplet population 180 represents droplets that are amplification-negative with each probe. The "mutant" droplet population 182 represents droplets that are amplification-positive with mutant probe 88 but not normal probe 86. The "normal+mutant" droplet population 184 represent droplets that are amplification-positive with both probes. Droplets of population 184 predominantly contain the normal allele only, but a small fraction of this population contains both types of allele by random colocalization during droplet formation.

The concentrations of mutant allele(s) and the normal allele can be calculated using the respective numbers of droplets in populations 180, 182, 184. The mutant-allele concentration can be calculated using the numbers of droplets in populations 180, 182, while excluding population 184 from the calculation (see Section III). Next, an expected number of droplets in population 184 containing both types of alleles can be calculated as the fraction of droplets in populations 180+182 that contain mutant allele, multiplied by the number of droplets in population 184. The expected number of mutant-containing droplets in population 184 can be subtracted from the total number of droplets in population 184 to obtain a number of normal-only droplets. The number of normal-only droplets and the total number of droplets in populations 180+182+184 can be used to calculate the concentration of the normal allele (see Section III).

Example 3. Selected Embodiments

This example describes selected embodiments of the present disclosure as a series of indexed paragraphs.

Paragraph A1. A method of detecting mutant alleles that alter a repetitive sequence present in a normal allele of a microsatellite locus, the method comprising: (i) forming a set of isolated volumes each containing a primer pair including a forward primer and a reverse primer configured to amplify the normal allele and each of the mutant alleles, a first probe having a label, and a second probe having a label, wherein each volume of only a subset of the volumes contains the normal allele, and wherein each volume of a plurality of the volumes contains none of the mutant alleles; (ii) generating amplicon using the primer pair; and (iii) collecting amplification data from the label of each probe; wherein the strand of the first probe and the strand of the second probe competitively hybridize at a similar efficiency with amplicon corresponding to the normal allele, wherein the strand of the second probe is configured to outcompete the strand of the first probe for hybridization with amplicon corresponding to each of the mutant alleles, and wherein a strand of the first probe, relative to a strand of the second probe, base-pairs with more nucleotides of the repetitive sequence when hybridized with the normal allele.

Paragraph A2. The method of paragraph A1, wherein isolated volumes that are indicated to be amplification-positive in the data by the label of the second probe but not the label of the first probe represent one or more of the mutant alleles.

Paragraph A3. The method of paragraph A2, wherein isolated volumes that are indicated to be amplification-positive in the data by the label of the first probe and the label of the second probe represent the normal allele of the locus.

Paragraph A4. The method of any of paragraphs A1 to A3, wherein the primer pair defines a target region of the locus, and wherein each probe is configured to hybridize with the target region intermediate binding sites for the forward and reverse primers.

Paragraph A5. The method of any of paragraphs A1 to A4, wherein the mutant alleles include a plurality of deletion alleles, each of which is missing a different number of nucleotides from the repetitive sequence of the normal allele.

Paragraph A6. The method of any of paragraphs A1 to A5, wherein the strand of the first probe forms at least six base pairs with the repetitive sequence when hybridized with the normal allele, and wherein, optionally, the strand of the first probe forms 1, 2, 3, 4, or more base pairs with a flanking sequence adjacent the repetitive sequence at one or both ends of the repetitive sequence.

Paragraph A7. The method of any of paragraphs A1 to A6, wherein the strand of the first probe forms at least 8, 10, 12, or 15 consecutive base pairs with the repetitive sequence when hybridized with the normal allele.

Paragraph A8. The method of any of paragraphs A1 to A7, wherein the strand of the first probe, when hybridized with the normal allele, forms base pairs with more than one-half of the nucleotides constituting a strand of the repetitive sequence.

Paragraph A9. The method of any of paragraphs A1 to A8, wherein the strand of the first probe, when hybridized with the normal allele, forms base pairs with more than three-fourths of the nucleotides constituting a strand of the repetitive sequence.

Paragraph A10. The method of any of paragraphs A1 to A9, wherein the strand of the first probe, when hybridized with the normal allele, forms base pairs with at least 90% of the nucleotides constituting a strand of the repetitive sequence.

Paragraph A11. The method of any of paragraphs A1 to A10, wherein the repetitive sequence includes a mononucleotide sequence of at least 6, 8, 10, or 12 nucleotides.

Paragraph A12. The method of any of paragraphs A1 to A11, wherein the strand of the second probe hybridized with the normal allele forms base pairs with less than one-half of the nucleotides constituting a strand of the repetitive sequence of the normal allele.

Paragraph A13. The method of any of paragraphs A1 to A12, wherein the strand of the second probe hybridized with the normal allele forms base pairs with less than one-fourth of the nucleotides constituting a strand of the repetitive sequence of the normal allele.

Paragraph A14. The method of any of paragraphs A1 to A13, further comprising a step of enumerating (a) volumes that are amplification-positive with the second probe but not the first probe to obtain an alpha value and/or (b) volumes that are amplification-negative with both probes to obtain a beta value.

Paragraph A15. The method of paragraph A14, further comprising a step of calculating a mutant allele concentration using the alpha value and/or the beta value.

Paragraph A16. The method of paragraph A15, wherein the step of calculating a mutant allele concentration uses Poisson statistics, with a sum of the alpha value and the beta value as a total number of volumes.

Paragraph A17. The method of any of paragraphs A1 to A16, wherein the step of collecting amplification data includes a step of detecting photoluminescence from the label of each probe, further comprising a step of assigning individual volumes as amplification-positive or amplification-negative with respect to each probe based on a step of comparing the intensity of the detected photoluminescence with one or more thresholds.

Paragraph A18. The method of any of paragraphs A1 to A17, wherein the strand of the first probe and the strand of the second probe are configured to create respective duplexes with the normal allele that have about the same melting temperature, optionally being different from one another by no more than about one degree or two degrees Celsius.

Paragraph A19. The method of any of paragraphs A1 to A18, wherein each of the first and second probes is a dual-strand probe including a pair of strands that hybridize with one another.

Paragraph A20. The method of paragraph A19, wherein the amplification data is collected at a detection temperature, wherein the pair of strands of each probe hybridize with one another to create a duplex having a melting temperature that is greater than the detection temperature and that is less than a temperature of primer annealing and/or extension during the step of generating amplicon.

Paragraph A21. The method of paragraph A19 or A20, wherein one strand, relative to the other strand, of the pair of strands of each probe hybridizes more stably with the amplicon, and wherein the one strand of the first probe and the one strand of the second probe competitively hybridize with amplicon during the step of generating amplicon.

Paragraph A22. The method of any of paragraphs A19 to A21, wherein one of the strands of each probe is labeled with a photoluminophore, and wherein the other of the strands of the probe is labeled with a quencher for the photoluminophore.

Paragraph A23. The method of any of paragraphs A1 to A22, wherein at least one of the probes is a single-strand probe.

Paragraph A24. The method of any of paragraphs A1 to A23, wherein the isolated volumes are droplets.

Paragraph A25. The method of paragraph A24, wherein the droplets have an average size of less than about 500 nL, 100 nL, 10 nL, or 1 nL.

Paragraph A26. The method of paragraph A24 or A25, wherein each of the droplets is encapsulated by an immiscible liquid.

Paragraph A27. The method of any of paragraphs A1 to A26, wherein the step of forming a set of isolated volumes includes a step of creating a mixture including the primer pair, the first and second probes, and a sample that provides the alleles, and a step of dividing the mixture into the isolated volumes.

Paragraph A28. The method of any of paragraphs A1 to A27, wherein the microsatellite locus is selected from the group consisting of BAT25, BAT26, NR21, NR24, and MONO27.

Paragraph A29. The method of any of paragraphs A1 to A28, further comprising a step of determining whether the microsatellite locus is unstable using the amplification data.

Paragraph A30. The method of paragraph A29, wherein step of determining includes a step of obtaining a mutant allele level using the amplification data and a step of comparing the mutant allele level with a predetermined threshold.

Paragraph A31. The method of paragraph A30, wherein the method is performed with the same sample for each of a plurality of different microsatellite loci, further comprising a step of determining a presence or degree of microsatellite instability for the sample based on how many of the loci are determined to be unstable for the sample.

Paragraph A32. The method of paragraph A31, wherein the sample is isolated from a subject, optionally the sample being a cancer-associated sample, such as a tumor sample, further comprising a step of administering at least one immunotherapeutic agent to the subject based on the step of determining a presence or degree of microsatellite instability.

Paragraph A33. The method of paragraph A32, wherein the at least one immunotherapeutic agent includes a checkpoint inhibitor.

Paragraph A34. The method of paragraph A33, wherein the checkpoint inhibitor is pembrolizumab.

Paragraph A35. The method of any of paragraphs A1 to A34, wherein each of the first probe and the second probe includes a photoluminophore, wherein the step of collecting amplification data includes a step of detecting photoluminescence from the photoluminophore of each of the probes, and wherein, optionally, the photoluminophore of the first probe has the same chemical structure as the photoluminophore of the second probe.

Paragraph A36. The method of any of paragraphs A1 to A35, wherein the strand of the first probe and the strand of the second probe form respective duplexes when hybridized with the normal allele, and wherein the melting temperature of each respective duplex is about the same as or above a temperature at which the step of generating amplicon is performed.

Paragraph A37. The method of paragraph A36, wherein the step of generating amplicon includes a step of thermally cycling a plurality of the isolated volumes through a range of temperatures, and wherein the melting temperature of each respective duplex is about the same as or above a minimum temperature of the range of temperatures.

Paragraph A38. The method of paragraph A37, wherein the step of generating amplicon includes a step of thermally cycling a plurality of the isolated volumes between a denaturation temperature and an annealing/extension temperature, and wherein the melting temperature of each respective duplex is about the same as or above the annealing/extension temperature.

Paragraph A39. The method of any of paragraphs A1 to A38, wherein each of the probes has a pair of strands that hybridize with one another to form a duplex, and wherein the melting temperature of the duplex is below a minimum temperature at which the step of generating amplicon is performed.

Paragraph A40. The method of any of paragraphs A1 to A39, wherein the step of generating amplicon includes a step of thermally cycling a plurality of the isolated volumes through a range of temperatures, and wherein the melting temperature of a duplex formed by the strand of the first probe hybridized with the normal allele is below a minimum temperature of the range of temperatures.

Paragraph A41. The method of paragraph A40, wherein the first probe is a molecular beacon probe.

Paragraph A42. The method of any of paragraphs A1 to A41, wherein the normal allele has a random distribution among the isolated volumes.

Paragraph A43. The method of any of paragraphs A1 to A42, wherein only one of the mutant alleles is present in the isolated volumes.

Paragraph A44. The method of any of paragraphs A1 to A43, wherein the mutant alleles span a range of different deletion sizes of at least 5, 8, 10, 12, or 15 nucleotides.

Paragraph A45. The method of any of paragraphs A1 to A44, further including any limitation or combination of limitations recited in any other indexed paragraphs of Example 3.

Paragraph B1. A method of detecting mutant alleles that alter a repetitive sequence present in a normal allele of a microsatellite locus, the method comprising: (i) forming a set of isolated volumes each including one or more forward primers and a reverse primer to amplify at least one target region of the locus, a label, and a competitor, wherein each volume of only a subset of the volumes contains the normal allele, wherein each volume of a plurality of the volumes contains none of the mutant alleles; (ii) generating amplicon using the one or more forward primers and the reverse primer, wherein the competitor outcompetes each forward primer for hybridization with the normal allele, wherein each forward primer is configured to outcompete the competitor for hybridization with each of the mutant alleles, and wherein the competitor, relative to each forward primer, base-pairs with more nucleotides of the repetitive sequence when hybridized with the normal allele; and (iii) collecting amplification data from the label, which reports generation of the amplicon.

Paragraph B2. The method of paragraph B1, wherein isolated volumes that are indicated to be amplification-positive in the data by the label represent one or more of the mutant alleles.

Paragraph B3. The method of paragraph B1 or B2, wherein each isolated volume includes a probe, and wherein the probe includes the label and a forward primer of the one or more forward primers.

Paragraph B4. The method of paragraph B3, wherein the probe is a dual-strand probe, and wherein the forward primer includes a photoluminophore, a quencher for the photoluminophore, or both the photoluminophore and the quencher.

Paragraph B5. The method of paragraph B3, wherein the probe is an alpha probe, and wherein each volume includes a beta probe comprising a label and the competitor.

Paragraph B6. The method of paragraph B5, wherein the beta probe is a dual-strand probe.

Paragraph B7. The method of paragraph B5 or B6, wherein isolated volumes that are indicated to be amplification-positive in the data by the label of the alpha probe but not the label of the beta probe represent one or more of the mutant alleles.

Paragraph B8. The method of any of paragraphs B1 to B7, wherein the one or more forward primers include a plurality of different forward primers, and wherein each of the different forward primers base-pairs with a different number of nucleotides of the repetitive sequence.

Paragraph B9. The method of any of paragraphs B1 to B8, wherein each of the isolated volumes when formed includes a probe comprising the label, and wherein the probe is configured to hybridize with the normal allele and the mutant alleles with equal affinity.

Paragraph B10. The method of paragraph B9, wherein the probe does not overlap the repetitive sequence.

Paragraph B11. The method of paragraph B10, wherein the probe is hydrolyzed preferentially in isolated volumes containing one of the mutant alleles relative to isolated volumes containing the normal allele.

Paragraph B12. The method of any of paragraphs B1 to B11, wherein each of the isolated volumes includes an intercalating dye that is the label.

Paragraph B13. The method of any of paragraphs B1 to B12, wherein each of the isolated volumes includes a polymerase enzyme that extends the one or more forward primers and the reverse primer during the step of generating amplicon, and wherein the competitor is configured to be non-extendable by the polymerase enzyme.

Paragraph B14. The method of any of paragraphs B1 to B13, further comprising a step of enumerating volumes that are amplification-positive.

Paragraph B15. The method of any of paragraphs B1 to B14, wherein each forward primer and the competitor form respective duplexes when hybridized with the normal allele, and wherein the melting temperature of each respective duplex is above a temperature at which the step of generating amplicon is performed.

Paragraph B16. The method of paragraph B15, wherein the step of generating amplicon includes a step of thermally cycling a plurality of the isolated volumes through a range of temperatures, and wherein the melting temperature of each respective duplex is above a minimum temperature of the range of temperatures.

Paragraph B17. The method of any of paragraphs B1 to B16, further including any limitation or combination of limitations recited in any other indexed paragraphs of Example 3.

Paragraph C1. A method of detecting mutant alleles that alter a repetitive sequence present in a normal allele of a microsatellite locus, the method comprising: (i) forming a set of isolated volumes each including a primer pair including a forward primer and a reverse primer configured to amplify a target region of the locus, a label, and a competitor, wherein each volume of only a subset of the volumes contains the target region from the normal allele, and wherein each volume of a plurality of the volumes does not contain the target region from any of the mutant alleles, wherein the competitor is configured to compete at a similar efficiency with, or outcompete, a reagent present in the volumes for hybridization with the normal allele, wherein the reagent is configured to outcompete the competitor for hybridization with each of the mutant alleles, wherein the competitor, relative to the reagent, base-pairs with more nucleotides of the repetitive sequence when hybridized with the normal allele, and wherein the reagent is the forward primer and/or a strand of a probe, the probe including the label; (ii) generating amplicon using the primer pair; and (iii) collecting amplification data from the label, which reports generation of the amplicon.

Paragraph C2. The method of paragraph C1, wherein the competitor competes at a similar efficiency with the reagent for hybridization with the normal allele.

Paragraph C3. The method of paragraph C1 or C2, wherein each volume when formed contains a probe, and wherein a strand of the probe is the reagent.

Paragraph C4. The method of paragraph C3, wherein the probe and the forward primer are different from one another.

Paragraph C5. The method of paragraph C3 or C4, wherein the strand of the probe is configured to hybridize with the target region intermediate respective binding sites for the forward and reverse primers.

Paragraph C6. The method of any of paragraphs C3 to C5, wherein the probe is a dual-strand probe including a pair of strands that base-pair with one another, and wherein one strand of the pair of strands is the reagent.

Paragraph C7. The method of paragraph C6, wherein the one strand includes the label.

Paragraph C8. The method of paragraph C6, wherein the other strand of the pair of strands includes the label.

Paragraph C9. The method of any of paragraphs C2 to C8, wherein the competitor and the reagent hybridize with the normal allele to create respective duplexes having about the same melting temperature, such as within about one degree or two degrees Celsius of one another.

Paragraph C10. The method of any of paragraphs C3 to C9, wherein the probe is a second probe, wherein each volume includes a first probe including the competitor and a label, and wherein amplification data is collected from the label of each probe.

Paragraph C11. The method of paragraph C10, wherein isolated volumes that are indicated to be amplification-positive in the data by the label of the second probe but not the label of the first probe represent one or more of the mutant alleles.

Paragraph C12. The method of paragraph C11, wherein isolated volumes that are indicated to be amplification-positive in the data by the label of the first probe and the label of the second probe represent the normal allele of the locus.

Paragraph C13. The method of any of paragraphs C1 to C12, wherein the reagent is the forward primer, and wherein each of the isolated volumes when formed includes a probe comprising the label and the forward primer.

Paragraph C14. The method of paragraph C13, wherein the probe is a dual-strand probe including a pair of strands, and wherein one strand of the pair of strands is the forward primer.

Paragraph C15. The method of paragraph C14, wherein the one strand includes the label.

Paragraph C16. The method of paragraph C14, wherein the other strand of the pair of strands includes the label.

Paragraph C17. The method of any of paragraphs C13 to C16, wherein isolated volumes that are indicated to be amplification-positive in the data by the label of the probe represent one or more of the mutant alleles.

Paragraph C18. The method of any of paragraphs C13 to C17, wherein the probe is a second probe comprising a label, wherein each of the isolated volumes when formed includes a first probe comprising a label, wherein the first probe includes the competitor, and wherein amplification data is collected from the label of the first probe and the label of the second probe.

Paragraph C19. The method of paragraph C18, wherein isolated volumes that are indicated to be amplification-positive in the data by the label of the first probe represent the normal allele of the locus.

Paragraph C20. The method of any of paragraphs C13 to C19, wherein the primer pair is a second primer pair, wherein the forward primer is a second forward primer, and wherein the competitor is a first forward primer that forms a first primer pair with the reverse primer.

Paragraph C21. The method of any of paragraphs C13 to C20, wherein the competitor is unlabeled, and/or wherein no amplification data is collected from a label of a probe that includes the competitor.

Paragraph C22. The method of any of paragraphs C13 to C21, wherein the competitor outcompetes the forward primer for hybridization with the normal allele.

Paragraph C23. The method of any of paragraphs C1 to C22, wherein the competitor is not extended during the step of generating amplicon, and wherein the reagent is the forward primer and does not include a label from which amplification data is collected.

Paragraph C24. The method of paragraph C23, wherein each of the isolated volumes when formed includes a plurality of different forward primers, wherein the competitor is configured to outcompete each forward primer for hybridization with the normal allele, and wherein each forward primer is configured to outcompete the competitor for hybridization with each of the mutant alleles.

Paragraph C25. The method of paragraph C24, wherein each of the different forward primers base-pairs with a different number of nucleotides of the repetitive sequence.

Paragraph C26. The method of paragraph C24, wherein each of the isolated volumes includes a probe comprising the label, and wherein the probe is configured to hybridize with the normal allele and the mutant alleles with equal affinity.

Paragraph C27. The method of paragraph C26, wherein isolated volumes that are indicated to be amplification-positive in the data by the label of the probe represent one or more of the mutant alleles.

Paragraph C28. The method of paragraph C26, wherein the probe hybridizes with amplicon corresponding to the target region without base-pairing with any nucleotides of the repetitive sequence.

Paragraph C29. The method of paragraph C26, wherein the probe is hydrolyzed preferentially in isolated volumes containing one of the mutant alleles relative to isolated volumes containing the normal allele.

Paragraph C30. The method of paragraph C24, wherein each of the isolated volumes includes an intercalating dye that provides the label.

Paragraph C31. The method of any of paragraphs C1 to C30, wherein the competitor forms at least six base pairs with the repetitive sequence when hybridized with the normal allele.

Paragraph C32. The method of paragraph C31, wherein the competitor forms at least ten consecutive base pairs with the repetitive sequence when hybridized with the normal allele.

Paragraph C33. The method of any of paragraphs C1 to C32, wherein the competitor, when hybridized with the normal allele, forms base pairs with more than one-half of the nucleotides constituting a strand of the repetitive sequence of the normal allele.

Paragraph C34. The method of any of paragraphs C1 to C33, wherein the competitor, when hybridized with the normal allele, forms base pairs with more than three-fourths of the nucleotides constituting a strand of the repetitive sequence of the normal allele.

Paragraph C35. The method of any of paragraphs C1 to C34, wherein the competitor, when hybridized with the normal allele, forms base pairs with at least 90% of the nucleotides constituting a strand of the repetitive sequence of the normal allele.

Paragraph C36. The method of any of paragraphs C1 to C35, wherein the repetitive sequence includes a mononucleotide sequence of at least 6, 8, 10, or 12 nucleotides.

Paragraph C37. The method of paragraph C36, wherein the mononucleotide sequence of the repetitive sequence is at least 15 nucleotides in length.

Paragraph C38. The method of any of paragraphs C1 to C37, wherein the reagent hybridized with the normal allele forms base pairs with less than one-half of the nucleotides constituting a strand of the repetitive sequence of the normal allele.

Paragraph C39. The method of any of paragraphs C1 to C38, wherein the reagent hybridized with the normal allele forms base pairs with less than one-fourth of the nucleotides constituting a strand of the repetitive sequence of the normal allele.

Paragraph C40. The method of any of paragraphs C1 to C39, wherein the label includes a photoluminophore.

Paragraph C41. The method of paragraph C40, wherein each of the isolated volumes when formed includes a probe comprising the photoluminophore and at least one quencher therefor.

Paragraph C42. The method of paragraph C41, wherein the photoluminophore and a quencher are covalently attached to one another when the isolated volumes are formed.

Paragraph C43. The method of paragraph C41, wherein the photoluminophore and a quencher are attached to respective complementary strands of the probe when the isolated volumes are formed.

Paragraph C44. The method of any of paragraphs C1 to C43, wherein the isolated volumes are droplets.

Paragraph C45. The method of paragraph C44, wherein each of the droplets is encapsulated by an immiscible liquid.

Paragraph C46. The method of any of paragraphs C1 to C45, wherein each of the isolated volumes has an average size of less than about 500 nL, 100 nL, 10 nL, or 1 nL.

Paragraph C47. The method of any of paragraphs C1 to C46, wherein the step of forming a set of isolated volumes includes a step of creating a mixture including the primer pair, the label, the competitor, and a sample that provides the target region, and a step of dividing the mixture to form the isolated volumes.

Paragraph C48. The method of any of paragraphs C1 to C47, wherein the microsatellite locus is selected from the group consisting of BAT25, BAT26, NR21, NR24, and MONO27.

Paragraph C49. The method of any of paragraphs C1 to C48, wherein the step of collecting amplification data is performed at a detection temperature, wherein each isolated volume when formed includes a dual-strand probe having a melting temperature greater than the detection temperature, and wherein one strand of the dual-strand probe is the reagent.

Paragraph C50. The method of paragraph C49, wherein the step of generating amplicon is performed at least in part at an annealing temperature and/or an extension temperature, and wherein the melting temperature is below the annealing temperature and/or the extension temperature.

Paragraph C51. The method of any of paragraphs C1 to C50, further comprising a step of enumerating volumes representing one or more of the mutant alleles using the amplification data.

Paragraph C52. The method of paragraph C51, wherein the target region is provided by a sample, further comprising a step of determining whether the microsatellite locus of the sample is unstable based on the step of enumerating.

Paragraph C53. The method of paragraph C52, wherein step of determining includes a step of comparing a level of mutant alleles of the locus with a predetermined threshold.

Paragraph C54. The method of paragraph C52, wherein the method is performed with the sample for each of a plurality of different microsatellite loci, further comprising a step of diagnosing microsatellite instability based on how many of the loci, if any, are determined to be unstable.

Paragraph C55. The method of paragraph C52, wherein the sample is isolated from a subject, further comprising a step of administering at least one immunotherapeutic agent to the subject based on the step of diagnosing.

Paragraph C56. The method of paragraph C55, wherein the at least one immunotherapeutic agent includes a checkpoint inhibitor.

Paragraph C57. The method of paragraph C56, wherein the checkpoint inhibitor is pembrolizumab.

Paragraph C58. The method of any of paragraphs C1 to C57, further including any limitation or combination of limitations recited in any other indexed paragraphs of Example 3.

Paragraph D1. A composition for detecting genetic instability that alters a repetitive sequence present in a normal allele of a microsatellite locus, the composition comprising: a set of isolated volumes encapsulated by an immiscible liquid, each volume including a primer pair including a forward primer and a reverse primer to amplify a target region of the locus, a label, a competitor, and a polymerase enzyme, wherein each volume of only a subset of the volumes contains the normal allele, and wherein each volume of a plurality of the volumes contains none of the mutant alleles; wherein the competitor is configured to compete at a similar efficiency with, or outcompete, a reagent in the volumes for hybridization with the normal allele, wherein the reagent is configured to outcompete the competitor for hybridization with each of the mutant alleles, wherein the competitor, relative to the reagent, base-pairs with more nucleotides of the repetitive sequence when hybridized with the normal allele, and wherein the reagent is the forward primer and/or a strand of a probe, the probe comprising the label.

Paragraph E1. A method of detecting mutant alleles that alter a repetitive sequence present in a normal allele of a microsatellite locus, the method comprising: (i) forming a set of isolated volumes each containing a primer pair including a forward primer and a reverse primer configured to amplify the normal allele and each of the mutant alleles, a competitor, and a probe including a label; (ii) generating amplicon using the primer pair; and collecting amplification data from the label of the probe, which reports generation of the amplicon; wherein the competitor competes similarly with, or outcompetes, a strand of the probe for hybridization with amplicon corresponding to the normal allele, wherein the strand of the probe is configured to outcompete the competitor for hybridization with amplicon corresponding to each of the mutant alleles, and wherein the competitor, relative to the strand of the probe, base-pairs with more nucleotides of the repetitive sequence when hybridized with the normal allele.

Paragraph E2. The method of paragraph E1, further comprising a step of enumerating volumes representing one or more of the mutant alleles using the amplification data.

Paragraph E3. The method of paragraph E1 or E2, wherein the probe is not a primer.

Paragraph E4. The method of paragraph E1, wherein the probe includes the forward primer.

Paragraph E5. The method of paragraph E1, wherein the probe is a second probe, wherein the competitor is included in a first probe comprising a label, and wherein amplification data is collected from the label of each probe.

Paragraph E6. The method of paragraph E5, further comprising a step of enumerating volumes that are amplification-positive with the second probe and represent one or more of the mutant alleles.

Paragraph E7. The method of paragraph E6, further comprising a step of enumerating volumes that are amplification-positive with the first probe and represent the normal allele.

Paragraph E8. The method of paragraph E1, wherein the competitor is unlabeled. Paragraph E9. The method of any of paragraphs E1 to E8, further including any limitation or combination of limitations recited in any other indexed paragraphs of Example 3.

Paragraph F1. A method of detecting mutant alleles that alter a repetitive sequence present in a normal allele of a microsatellite locus, the method comprising: (i) forming a set of isolated volumes each including a probe including a forward primer and a label, a primer pair including the forward primer and a reverse primer to amplify a target region of the locus, and a competitor, wherein the competitor is configured to outcompete the forward primer for hybridization with the normal allele, wherein the forward primer is configured to outcompete the competitor for hybridization with each of the mutant alleles, and wherein the competitor, relative to the forward primer, base-pairs with more nucleotides of the repetitive sequence when hybridized with the normal allele; (ii) generating amplicon using the primer pair; and (iii) collecting amplification data from the label, which reports generation of the amplicon.

Paragraph F2. The method of paragraph F1, wherein the probe is a dual-strand probe.

Paragraph F3. The method of paragraph F2, wherein the label includes a photoluminophore that is covalently attached to a strand of the forward primer.

Paragraph F4. The method of paragraph F2, wherein the forward primer includes a quencher, and wherein the label includes a photoluminophore that is covalently attached to a strand of the probe that hybridizes with the forward primer.

Paragraph F5. The method of paragraph F1, wherein the primer pair is a second primer pair, the forward primer is a second forward primer, and the probe is a second dual-strand probe, wherein the competitor is a first forward primer that forms a first primer pair with the reverse primer, and wherein the competitor is included in a first dual-strand probe comprising a label.

Paragraph F6. The method of paragraph F5, wherein the step of collecting amplification data includes a step of collecting amplification data from the label of each dual-strand probe, further comprising a step of enumerating volumes that are amplification-positive with the first dual-strand probe.

Paragraph F7. The method of any of paragraphs F1 to F6, further including any limitation or combination of limitations recited in any other indexed paragraphs of Example 3.

Paragraph G1. A method of evaluating a sample for microsatellite instability, the method comprising: (i) amplifying a target region of each a plurality of microsatellite loci in one or more sets of isolated volumes; (ii) collecting amplification data from a respective label reporting amplification of each target region; (iii) enumerating a respective number of volumes that are amplification-positive for the target region of each microsatellite locus; (iv) determining an instability of each of the microsatellite loci using the respective number for the locus; and (v) assigning a degree of microsatellite instability to the sample based on the determined instability of each of the microsatellite loci.

Paragraph G2. The method of paragraph G1, further including any limitation or combination of limitations recited in any other indexed paragraphs of Example 3.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first (or alpha), second (or beta), or third (or gamma), for identified elements are used to distinguish between the elements, and do not indicate a particular position or order of such elements, unless otherwise specifically stated. The present disclosure incorporates other material by reference. If any conflict or ambiguity in the meaning of a term results from incorporation by reference, the meaning provided by text that is present literally herein should govern interpretation of the term.

I claim:

1. A method of detecting mutant alleles that alter a repetitive sequence present in a normal allele of a microsatellite locus, the method comprising:
forming a set of isolated volumes each containing (i) a primer pair including a forward primer and a reverse primer configured to amplify the normal allele and each of the mutant alleles, (ii) a first probe having a label, and (iii) a second probe having a label, wherein each isolated volume of only a subset of the isolated volumes contains the normal allele, and wherein each isolated volume of a plurality of the isolated volumes contains none of the mutant alleles;
generating amplicon using the primer pair; and
collecting amplification data from the label of each probe;
wherein a strand of the first probe and a strand of the second probe competitively hybridize at a similar efficiency with amplicon corresponding to the normal allele, wherein the strand of the second probe is configured to outcompete the strand of the first probe for hybridization with amplicon corresponding to each of the mutant alleles,
wherein the strand of the first probe hybridizes with the entire repetitive sequence of the normal allele, and wherein the strand of the second probe hybridizes with only a portion of the repetitive sequence of the normal allele,
wherein isolated volumes that are indicated to be amplification-positive in the amplification data by the label of the first probe and the label of the second probe represent the normal allele, and wherein isolated volumes that are indicated to be amplification-positive in the amplification data by the label of the second probe but not the label of the first probe represent one or more of the mutant alleles.

2. The method of claim 1, wherein the mutant alleles include a plurality of deletion alleles, each of which is missing a different number of nucleotides from the repetitive sequence of the normal allele.

3. The method of claim 1, wherein the repetitive sequence includes a mononucleotide sequence of at least eight nucleotides.

4. The method of claim 1, wherein at least one of the first and second probes is a dual-strand probe including a pair of strands that hybridize with one another.

5. The method of claim 1, wherein the microsatellite locus is selected from the group consisting of BAT25, BAT26, NR21, NR24, and MON027.

6. The method of claim 1, further comprising a step of determining whether the microsatellite locus is unstable using the amplification data.

7. The method of claim 6, wherein the step of determining includes a step of obtaining a mutant allele level using the amplification data and a step of comparing the mutant allele level with a predetermined threshold.

8. The method of claim 7, wherein the method is performed with the same sample for each of a plurality of different microsatellite loci, further comprising a step of determining a presence or degree of microsatellite instability for the sample based on how many of the loci are determined to be unstable for the sample.

9. The method of claim 8, wherein the sample is isolated from a subject, optionally the sample being a cancer-associated sample, such as a tumor sample, further comprising a step of administering at least one immunotherapeutic agent to the subject based on the step of determining a presence or degree of microsatellite instability.

10. The method of claim 9, wherein the at least one immunotherapeutic agent includes a checkpoint inhibitor.

11. The method of claim 10, wherein the checkpoint inhibitor is pembrolizumab.

12. The method of claim 1, wherein only one of the mutant alleles is present in the isolated volumes.

13. The method of claim 1, wherein the mutant alleles span a range of different deletion sizes, and wherein the range is at least eight nucleotides.

14. A method of detecting mutant alleles that alter a repetitive sequence present in a normal allele of a microsatellite locus, the method comprising:
forming a set of isolated volumes each including (i) one or more forward primers and a reverse primer to amplify at least one target region of the locus, (ii) a label, and (iii) a competitor, wherein each isolated volume of only a subset of the isolated volumes contains the normal allele, wherein each isolated volume of a plurality of the isolated volumes contains none of the mutant alleles;
generating amplicon using the one or more forward primers and the reverse primer, wherein the competitor outcompetes each forward primer for hybridization with the normal allele, wherein each forward primer is configured to outcompete the competitor for hybridization with each of the mutant alleles, wherein each forward primer base-pairs with a first end but not a second end of an altered form of the repetitive sequence when hybridized with a mutant allele, and wherein the competitor base-pairs with both ends of the repetitive sequence when hybridized with the normal allele; and collecting amplification data from the label, which reports generation of the amplicon.

15. A method of detecting mutant alleles that alter a repetitive sequence present in a normal allele of a microsatellite locus, the method comprising:

forming a set of isolated volumes each containing (i) a primer pair including a forward primer and a reverse primer configured to amplify the normal allele and each of the mutant alleles, (ii) a competitor, and (iii) a probe including a label;

generating amplicon using the primer pair; and collecting amplification data from the label of the probe, which reports generation of the amplicon;

wherein the competitor competes similarly with, or outcompetes, a strand of the probe for hybridization with amplicon corresponding to the normal allele, wherein the strand of the probe is configured to outcompete the competitor for hybridization with amplicon corresponding to each of the mutant alleles, wherein the strand of the probe base-pairs with a first end but not a second end of an altered form of the repetitive sequence when hybridized with amplicon corresponding to each mutant allele, and wherein the competitor base-pairs with both ends of the repetitive sequence when hybridized with amplicon corresponding to the normal allele.

16. The method of claim 15, wherein the probe is not a primer.

17. The method of claim 15, wherein the probe includes the forward primer.

\* \* \* \* \*

```
                             SEQUENCE LISTING

<160> NUMBER OF SEQ ID NOS: 6

<210> SEQ ID NO 1
<211> LENGTH: 51
<212> TYPE: DNA
<213> ORGANISM: Homo sapiens

<400> SEQUENCE: 1
gctactaaaa aaaaaaaaaa aaaaaaaaaa aaacatggca atggttttcc c          51

<210> SEQ ID NO 2
<211> LENGTH: 36
<212> TYPE: DNA
<213> ORGANISM: Artificial sequence
<220> FEATURE:
<223> OTHER INFORMATION: Synthetic

<400> SEQUENCE: 2
ctactaaaaa aaaaaaaaaa aaaaaaaaaa aacatg                           36

<210> SEQ ID NO 3
<211> LENGTH: 24
<212> TYPE: DNA
<213> ORGANISM: Artificial sequence
<220> FEATURE:
<223> OTHER INFORMATION: Synthetic

<400> SEQUENCE: 3
aaaaaacatg gcaatggttt tccc                                        24

<210> SEQ ID NO 4
<211> LENGTH: 28
<212> TYPE: DNA
<213> ORGANISM: Artificial sequence
<220> FEATURE:
<223> OTHER INFORMATION: Synthetic

<400> SEQUENCE: 4
ctactaaaaa catggcaatg gttttccc                                    28

<210> SEQ ID NO 5
<211> LENGTH: 31
<212> TYPE: DNA
<213> ORGANISM: Artificial sequence
<220> FEATURE:
```

```
<223> OTHER INFORMATION: Synthetic

<400> SEQUENCE: 5
ctactaaaaa aaaaaacatg gcaatggttt t                              31

<210> SEQ ID NO 6
<211> LENGTH: 32
<212> TYPE: DNA
<213> ORGANISM: Artificial sequence
<220> FEATURE:
<223> OTHER INFORMATION: Synthetic

<400> SEQUENCE: 6
ctactaaaaa aaaaaaaaa aacatggcaa tg                              32
```